US009458440B2

(12) United States Patent
Makinen et al.

(10) Patent No.: US 9,458,440 B2
(45) Date of Patent: Oct. 4, 2016

(54) PROTEINS FOR THE TREATMENT OF CELLULOSIC MATERIAL

(71) Applicant: Roal Oy, Rajamaki (FI)

(72) Inventors: Susanna Makinen, Layliainen (FI); Kari Juntunen, Espoo (FI); Alexandra Komander, Darmstadt (DE); Kim Langfelder, Darmstadt (DE); Jari Vehmaanpera, Klaukkala (FI); Terhi Puranen, Nurmijarvi (FI)

(73) Assignee: Roal Oy (FI)

( * ) Notice: Subject to any disclaimer, the term of this patent is extended or adjusted under 35 U.S.C. 154(b) by 0 days.

(21) Appl. No.: 13/911,223

(22) Filed: Jun. 6, 2013

(65) Prior Publication Data

US 2014/0045225 A1 Feb. 13, 2014

Related U.S. Application Data

(60) Provisional application No. 61/656,550, filed on Jun. 7, 2012.

(51) Int. Cl.
| | |
|---|---|
| C12N 9/42 | (2006.01) |
| C12P 19/14 | (2006.01) |
| C11D 3/386 | (2006.01) |
| D06M 15/15 | (2006.01) |
| D06M 16/00 | (2006.01) |

(52) U.S. Cl.
CPC ......... *C12N 9/2437* (2013.01); *C11D 3/38645* (2013.01); *C12P 19/14* (2013.01); *D06M 15/15* (2013.01); *D06M 16/003* (2013.01)

(58) Field of Classification Search
None
See application file for complete search history.

(56) References Cited

U.S. PATENT DOCUMENTS

| 2007/0072185 A1* | 3/2007 | Schnorr | C07K 14/37 435/6.16 |
| 2010/0299788 A1* | 11/2010 | Harris | C07K 14/37 800/295 |
| 2012/0083019 A1* | 4/2012 | Baidyaroy et al. | 435/99 |

(Continued)

FOREIGN PATENT DOCUMENTS

| WO | 94/07998 | 4/1994 |
| WO | 2005/074647 A2 | 8/2005 |
| WO | 2005/074656 A2 | 8/2005 |

(Continued)

OTHER PUBLICATIONS

Guo et al., "Protein tolerance to random amino acid change", Proceedings of the National Academy of Sciences USA, vol. 101, No. 5, pp. 9205-9210, 2004.*

(Continued)

*Primary Examiner* — Robert Mondesi
*Assistant Examiner* — Richard Ekstrom
(74) *Attorney, Agent, or Firm* — Banner & Witcoff, Ltd.

(57) ABSTRACT

The present invention discloses novel polypeptides and enzyme preparations containing them, which enhance the efficiency of the cellulosic degradation even at elevated temperatures. The polypeptides are produced by recombinant technology, and means for their production are described. The novel polypeptides are useful in processing biomass, and in biofuel, starch, textile, detergent, pulp and paper, food, feed or beverage industries. They may also be used e.g. in cleaning the interior of a dishwashing machine or for biofinishing or biostoning. The novel polypeptides are also useful in animal feed.

17 Claims, 2 Drawing Sheets

(56) References Cited

U.S. PATENT DOCUMENTS

| | | | |
|---|---|---|---|
| 2013/0095553 A1* | 4/2013 | Schooneveld-Bergmans et al. .................. | 435/196 |
| 2014/0033373 A1* | 1/2014 | Schooneveld-Bergmans et al. .................. | 800/306 |

FOREIGN PATENT DOCUMENTS

| | | |
|---|---|---|
| WO | 2007/071818 A1 | 6/2007 |
| WO | 2007/089290 A2 | 8/2007 |
| WO | 2008/140749 A2 | 11/2008 |
| WO | 2009/033071 A2 | 3/2009 |
| WO | 2009/085868 A1 | 7/2009 |
| WO | 2011/035027 A2 | 3/2011 |
| WO | 2011/080317 A2 | 7/2011 |
| WO | 2011126897 A2 | 10/2011 |
| WO | 2011/161459 A1 | 12/2011 |
| WO | 2011126897 A3 | 1/2012 |
| WO | 2012/024698 A1 | 2/2012 |
| WO | 2012021399 A1 | 2/2012 |
| WO | 2012/061517 A1 | 5/2012 |
| WO | 2012/068509 A1 | 5/2012 |
| WO | 2012058293 A1 | 5/2012 |
| WO | 2012068509 A1 | 5/2012 |

OTHER PUBLICATIONS

UniProt Accession No. Q2HGH1_CHAGB, published Mar. 21, 2006.*
UniProt Accession No. Q2GUS9_CHAGB, published Mar. 21, 2006.*
Badger, P.C.,"Ethanol From Cellulose: A General Review," J. Janick and A. Whipkey (eds.), Trends in new crops and new uses, 2002, pp. 17-21, ASHS Press, Alexandria, VA.
Bendtsen, Jannick Dyrlov, et al.,"Improved Prediction of Signal Peptides: SignalP 3.0," J Mol Biol., Jul. 2004, pp. 783-795, vol. 340, No. 4, Elsevier Ltd.
Coen, Donald M.,"Quantitation of Rare DNAs by PCR," The Polymerase Chain Reaction, Current Protocols in Molecular Biology, 2001, pp. 15.7.1-15.7.8, John Wiley & Sons, Inc.
Gellissen, Gerd,"Production of Recombinant Proteins—Novel Microbial and Eukaryotic Expression Systems," 2005, Wiley-VCH, Weinheim.
Henrissat, Bernard, et al.,"New families in the Classification of Glycosyl Hydrolases based on Amino Acid Sequence Similarities," Biochem. J., 1993, pp. 781-788, vol. 293, Great Britain.
Henrissat, Bernard,"A Classification of Glycosyl Hydrolases based on Amino Acid Sequence Similarities," Biochem. J., 1991, pp. 309-316, vol. 280, Great Britain.
Henrissat, Bernard, et al.,"Updating the Squence-based Classification of Glycosyl Hydrolases," Biochem. J., 1996, pp. 695-696, vol. 316, Great Britain.
Joutsjoki, Vesa V., et al.,"Transformation of Trichoderma Reesei with the Hormoconis Resinae Glucoamylase P (gamP) gene: Production of a Heterologous Glucoamylase by Trichoderma Reesei," Current Genetics, Sep. 1993, pp. 223-228 , vol. 24, Springer-Verlag.
Karhunen, Taina, et al.,"High Frequency One-step Gene Replacement in Trichoderma Reesei. I. Endoglucanase I Overproduction," Molecular and General Genetics MGG, Dec. 1993, pp. 515-522, vol. 241, No. 5-6, Springer-Verlag.
Needleman, Saul B., et al.,"A General Method Applicable to the Search for Similarities in the Amino Acid Sequence of Two Proteins," J Mol Biol., Mar. 1970, pp. 443-453, vol. 48, No. 3.

Nielsen, Henrik, et al.,"Prediction of Signal Peptides and Signal Anchors by a Hidden Markov Model," In Proceedings of the 6th International Conference on Intelligent Systems for Molecular Biology (ISMB 6), 1998, pp. 122-130, AAAI Press, Menlo Park, California.
Nielsen, Henrik, et al.,Identification of Prokaryotic and Eukaryotic Signal Peptides and Prediction of their Cleavage Sites, Protein Engineering, 1997, pp. 1-6, vol. 10, No. 1, Oxford University Press.
Paloheimo, Marja, et al.,"High-Yield Production of a Bacterial Xylanase in the Filamentous Fungus Trichoderma Reesei Requires a Carrier Polypeptide with an Intact Domain Structure," Applied and Environmental Microbiology, Dec. 2003, pp. 7073-7082, vol. 69, No. 12, American Society for Microbiology.
Penttila, Merja, et al.,"A Versatile Transformation System for the Celluloytic Filamentous Fungus Trichoderma Reesei," Gene, 1987, pp. 155-164, vol. 61, No. 2.
Raeder, U., et al.,"Rapid Preparation of DNA from Filamentous Fungi," Letters in Applied Microbiology, Feb. 1985, pp. 17-20, vol. 1.
Visser, Hans, et al.,"Development of a Mature Fungal Technology and Production Platform for Industrial Enzymes based on a Myceliophthora Thermophila Isolate, Previously known as Chrysosporium Lucknowense C1," Industrial Biotechnology, Jun. 2011, pp. 214-223, vol. 7, No. 3, Mary Ann Liebert, Inc.
Search Report for corresponding FI Application No. 20125623, issued Mar. 7, 2013.
Extended European Search Report re Corresponding Application 13800373.6 dated May 17, 2016.
Gusakov, Alexander V., "Alternatives to Trichoderma reesei in biofuel production", Trends in Biotechnology, Sep. 1, 2011, pp. 419-425, vol. 29, No. 9.
Voutilainen, Sanni P., et al, "Cloning, expression, and characterization of novel thermostable family 7 cellobiohydrolases", Biotechnology and Bioengineering, Oct. 1, 2008, pp. 515-528, vol. 101, No. 3, Wiley & Sons., Hoboken, NJ.
Summerbell, R.C., et al., "Acremonium phylogenetic overview and revision of Gliomastix, Sarocladium, and Trichothecium" Studies in Mycology, Mar. 1, 2011, pp. 139-162, vol. 68.
Harris, Paul V., et al., "Stimulation of Lignocellulosic Biomass Hydrolysis by Proteins of Glycoside Hydrolase Family 61: Structure and Function of a Large, Enigmatic Family", Studies in Mycology, vol. 68, Biochemistry, 2010, pp. 3305-3316, vol. 49.
Li, Xin, et al., "Structural Basis for Substrate Targeting and Catalysis by Fungal Polysaccharide Monooxygenases", Structure, Apr. 4, 2012, pp. 1051-1061, vol. 20, No. 4.
Beeson, William T., et al., "Oxidative Cleavage of Cellulose by Fungal Copper-Dependent Polysaccharide Monooxygenases", Journal of the American Chemical Society, Jan. 18, 2012, pp. 890-892, vol. 134, No. 2.
Berka, Randy M., et al., "Comparative genomic analysis of the thermophilic biomass-degrading fungi Myceliophthora thermophila and Thielavia terrestris" Nature Biotechnology, Jan. 1, 2011, pp. 922-927, vol. 29, No. 10.
Langston, James A., et al., "Oxidoreductive Cellulose Depolymerization by the Enzymes Cellobiose Dehydrogenase and Glycoside Hydrolase 61", Applied and Environmental Microbiology, Oct., 2011, pp. 1007-7015, vol. 77, No. 19.
Wilson, David B., "Processive and nonprocessive cellulases for biofuel production—lessons from bacterial genomes and structural analysis", Applied Microbiology and Biotechnology, Nov. 24, 2011, pp. 497-502, vol. 93, No. 2, Springer-Verlag, Berlin, DE.

* cited by examiner

SEQUENCE LISTING

<160> NUMBER OF SEQ ID NOS: 25

<210> SEQ ID NO 1
<211> LENGTH: 13
<212> TYPE: PRT
<213> ORGANISM: Acremonium thermophilium

```
<400> SEQUENCE: 1

Glu Asp Gly Tyr Asn Ser Gly Asn Trp Ala Thr Ser Lys
1               5                   10

<210> SEQ ID NO 2
<211> LENGTH: 14
<212> TYPE: PRT
<213> ORGANISM: Acremonium thermophilium

<400> SEQUENCE: 2

Asp Asn Ala Leu Thr Asp Ser Gly Leu Gly Asn Trp Phe Lys
1               5                   10

<210> SEQ ID NO 3
<211> LENGTH: 10
<212> TYPE: PRT
<213> ORGANISM: Acremonium thermophilium

<400> SEQUENCE: 3

Lys Gly Pro Thr Leu Ala Tyr Leu Lys Lys
1               5                   10

<210> SEQ ID NO 4
<211> LENGTH: 19
<212> TYPE: PRT
<213> ORGANISM: Acremonium thermophilium

<400> SEQUENCE: 4

Lys Lys Val Asp Asn Ala Leu Thr Asp Ser Gly Ile Gly Gly Gly Trp
1               5                   10                  15

Phe Lys Ile

<210> SEQ ID NO 5
<211> LENGTH: 18
<212> TYPE: PRT
<213> ORGANISM: Acremonium thermophilium

<400> SEQUENCE: 5

Arg His Thr Leu Thr Ser Gly Pro Asp Asp Val Met Asp Ala Ser His
1               5                   10                  15

Lys Gly

<210> SEQ ID NO 6
<211> LENGTH: 23
<212> TYPE: PRT
<213> ORGANISM: Melanocarpus albomyces

<400> SEQUENCE: 6

His Tyr Thr Leu Pro Arg Val Asn Ser Gly Ser Asp Trp Gln His Val
1               5                   10                  15

Arg Arg Ala Asp Asn Trp Gln
            20

<210> SEQ ID NO 7
<211> LENGTH: 13
<212> TYPE: PRT
<213> ORGANISM: Melanocarpus albomyces

<400> SEQUENCE: 7

Asn Gly Phe Val Gly Asp Val Asn Ser Pro Gln Leu Arg
1               5                   10
```

```
<210> SEQ ID NO 8
<211> LENGTH: 11
<212> TYPE: PRT
<213> ORGANISM: Melanocarpus albomyces

<400> SEQUENCE: 8

Val Asn Ser Gly Ser Asp Trp Gln His Val Arg
1               5                   10

<210> SEQ ID NO 9
<211> LENGTH: 12
<212> TYPE: PRT
<213> ORGANISM: Melanocarpus albomyces

<400> SEQUENCE: 9

Asn Ser Trp Gln Ala Asp Gly Ala Val Trp Phe Lys
1               5                   10

<210> SEQ ID NO 10
<211> LENGTH: 11
<212> TYPE: PRT
<213> ORGANISM: Melanocarpus albomyces

<400> SEQUENCE: 10

Pro Ser Asp Gly Gln Ser Ser Phe Gln Val Pro
1               5                   10

<210> SEQ ID NO 11
<211> LENGTH: 19
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 11
ggnccngayg aygtnatgg                                                 19

<210> SEQ ID NO 12
<211> LENGTH: 15
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 12
ngtngcccar ttncc                                                     15
```

<210> SEQ ID NO 13
<211> LENGTH: 17
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t

<400> SEQUENCE: 13
gngcngayaa ytggcar                                                    17

<210> SEQ ID NO 14
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 14
yttraaccan acngcnccrt cngc                                            24

<210> SEQ ID NO 15
<211> LENGTH: 18
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 15
acngayatha ayggntgg                                                   18

<210> SEQ ID NO 16
<211> LENGTH: 23
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)

```
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 16
ggnarrttng gdatnccrtc rtt                                              23

<210> SEQ ID NO 17
<211> LENGTH: 349
<212> TYPE: DNA
<213> ORGANISM: Acremonium thermophilium

<400> SEQUENCE: 17
ggccccgatg atgtgatgga tgctagccat aaaggtccca cactcgcgta tcttaaaaag      60
gtcgacaacg ccctgacgga cagtggtatt ggcggcggct ggtatgaggc tttttgaatt     120
tctcctgact ttgtccctcc acctgtctcc cattatctcc acatctccca atatttgagt     180
gtatatctct gctcgttgcc ctcgtatgga taagagggcg gagaatggag agagggaaaa     240
gaaggcatag cccatacaaa agagcgtaga cgagaccaag cgactaaaca cactttgag     300 caggttcaaa attcaggagg atggctacaa cagcggcaac tgggccacc                349

<210> SEQ ID NO 18
<211> LENGTH: 239
<212> TYPE: DNA
<213> ORGANISM: Melanocarpus albomyces

<400> SEQUENCE: 18
cttaaaccaa acagcgccat cggcctgcca cgagttgatg tcctggccgt cggggacgcg      60
ggcgaggtag aactgcatgg ggccggggtg gtagatgttg gggttgacgt ggtacgtgac     120
cgacgagccg gcagtcacgt tgagcgtctc ggggcgggc gagtggctgg actggaagca     180
gcggatctgg ggcgagtcga cgtcgccgac gaagccgttg tcctgccagt tatctgctc     239

<210> SEQ ID NO 19
<211> LENGTH: 860
<212> TYPE: DNA
<213> ORGANISM: Melanocarpus albomyces

<400> SEQUENCE: 19
ggaaagttgg gtatgccgtc gttccaatat gcccgcggcg ttgacatgcc cgggactaag      60
gggttcggtg tcattctcgg acgaactagc ggatctaggg gttggatgcc gagtgtcggt     120
cccctgtacc gatcgtgatg gacggttcct gggccgtata agtagtgagc gaggttccag     180
ctcctgtcac tggggcagca tcagcgcaac caagtttccc gtgcgacttg acgtcgaccc     240
aaagccacca tgaagctctc gctggcgtcc cttctggctg ccgccctctc tgtggagggg     300
cacgtcatct tccaggtgtg tctgcccagc tgaccggttt ccacgacgaa gacgatgaag     360
gtagctgacg ccagctgcag agactgtccg tgaacggcca ggaccaaggc gagctcaacg     420
gcctccgggc ccccaacaac aacaacccgg tgcaggatgt caacagccag aacatgatct     480
gcggccagcc cggtatact tcgcagaccg ttatcgacgt ccagcccggc gacaggctgg     540
gagcgtggta tcaacatgtc attggaggac ctcaattccc tggtgacccg gacacccga      600 tcgccgcctc gcacaagggc cccatcatgg tttaccttgc caaggtggac aacgccgcga     660
```

```
cggcgagctt gaacggcctg aaatggtatg cgattgcgag ccgagagacc atgctggatc    720
tccggtggtc aatactgtcg gcgttagcaa gagactgaca ggttaaatag gttcaagatc    780
tggcacgagg gctttgatac cagcacccgc acctgggccg ttgacaacct gatcaagaac    840
gacggcattc cgaacttacc                                                860

<210> SEQ ID NO 20
<211> LENGTH: 1472
<212> TYPE: DNA
<213> ORGANISM: Acremonium thermophilium

<400> SEQUENCE: 20
atgaagacct cgtccattct gacagcagcc tcggcggcaa cgttggcgtc tgctcatacg     60
attttcgtcc agcttcaatc cggaggcact acatacccctg tgtcctacgc catccgtgat   120
ccgacgtacg acggtcctat tacagatgtg acgtcgaacg acctagcctg caacggtgga   180
ccgaatccga caactccatc cgacaagatc atcaatgttg ccgccggatc aaccgtgcag   240
gcaatttgga ggcacactct tacctcagga cccgacgatg tcatggatgc tagccataaa   300
ggtcccacac tcgcgtatct taaaaaggtc gacaacgccc tgacggacag tggtattggc   360
ggcggctggt atgaggcttt ttgaatttct cctgactttg tccctccacc tgtctcccat   420
tatctccaca tctcccaata tttgagtgta tatctctgct cgttgccctc gtatggataa   480
gagggcggag aatggagaga gggaaaagaa ggcatagccc atacaaaaga gcgtagacga   540
gaccaagcga ctaaacaaca ctttgagcag gttcaaaatt caggaggatg ctacaacag    600 cggcaactgg gccacttcaa aggttatcaa taacggtggc tttcagaaca ttactattcc   660
tcagtgcatt gccccgggtc agtatcttct ccgcgccgag atgattgccc tgcatggcgc   720
cagctccccg ggtggtgctc aactttatgt gagtattctt ggccctgaga acgtccagca   780
gccggataag catgccgttg cggccaagtg tagcccggcg atgtgctatg ccggacacgt   840
tccgtgttcg ggcgacaaag gctgatgtag atcgcatgct gcaaacagat ggaatgtgct   900
caaatcaaca tcacgggagg tagcggctcc gtgacgccta ccacgtacag cattcccgga   960
atttacaagg tgagaggcta agctccgcta tcaaacatca tcttgaccag gaaagttgga  1020
gtaactctcg aaacttcaag gcaaacgacc ccggactact tatcaacatt tactctatga  1080
cgccttcgag cacctacgtt atcccaggta aggcccagaa ccgttttttga ccacaaattc  1140 tctaagccct tatttccttt gcattggtca tgccgtatat ccaatatatt ttgccgacaa  1200
ataatacagg tcccgacccc ttcacgtgca gcgctggagg caataaccct cccccctcaa  1260
atccaaccac gacactcgtt actgtaacga cgaagacaac gactacatcg gccaagacca  1320
cgactccacc atcgaatccc accccaccat ctggtggttg cacagccgcg caatgggctc  1380
agtgtggcgg gattggcttc acgggatgca ccacatgtgc ttcaggttac acatgtaaga  1440
ccatgaatga ctactactct caatgccagt ga                                 1472

<210> SEQ ID NO 21
<211> LENGTH: 891
<212> TYPE: DNA
<213> ORGANISM: Melanocarpus albomyces

<400> SEQUENCE: 21
atgaagctct cgctggcgtc ccttctggct gccgccctct ctgtggaggg gcacgccatc     60
ttccaggtgt gtctgcccag ctgaccggtt tccacgacga agacgatgaa ggtagctgac   120
```

```
gccagctgca gagactgtcc gtgaacggcc aggaccaagg cgagctcaac ggcctccggg      180
cccccaacaa caacaacccg gtgcaggatg tcaacagcca gaacatgatc tgcggccagc      240
ccgggtatac ttcgcagacc gttatcgacg tccagcccgg cgacaggctg ggagcgtggt      300
atcaacatgt cattggagga cctcaattcc ctggtgaccc ggacaacccg atcgccgcct      360
cgcacaaggg ccccatcatg gtttaccttg ccaaggtgga caacgccgcg acggcgagct      420
tgaacggcct gaaatggtat gcgattgcga gccgagagac catgctggat ctccggtggt      480
caatactgtc ggcgttagca agagactgac aggttaaata ggttcaagat ctggcacgag      540
ggctttgata ccagcacccg cacctgggcc gttgacaacc tgatcaagaa cgacggctgg      600
gtgtatttcg atctgcccca gtgcatcgct ccgggccact atctcatgcg ggttgagctt      660
ctggctctgc actcgccgg catgcccggg caggctcagt tctacacctc gtgcgcccag      720
atcaacgtcg gcggctctgg gtcgttcacg ccgtcccaga ccgtgagcat tccgggcgtg      780
tacagcgcca acgacccggg catcctcatc aacatctatg gtgcgcaggg ccagcccgac      840
aacaacggcc agccgtacag catcccggga ccggagccga tcacgtgcta a               891

<210> SEQ ID NO 22
<211> LENGTH: 733
<212> TYPE: DNA
<213> ORGANISM: Melanocarpus albomyces

<400> SEQUENCE: 22
atgctgccca aggctgtcct cctgctggca gctggcctcg gggccagcgc ccactacacg       60
ctcccccgcg tcaacagcgg ctctgactgg cagcacgtcc gcagggccga caactggcag      120
gacaacggct cgtcggcga cgtcaactcg ccccagatcc gctgcttcca gtccagccac      180
tcgcccgccc ccgagacgct caacgtgact gccggctcgt cggtcacgta ccacgtcaac      240
cccaacatct accaccccgg ccccatgcag ttctacctcg cccgcgtccc cgacggccag      300
gacatcaact cgtggcaggg cgagggtgcc gtgtggttca aggtctacca cgagcagccc      360
aactttggcc agcagctgac ctggcctagc aacggtacgg accgacaaaa tcgattcgag      420
aacagcgtgt gactgacccc ccgcaacagg ccagagctcg ttccaggtgc ccatcccgag      480
ctgcatccgg cccggctact acctgctccg cgccgagcac atcgccctgc acgtggccca      540
gagccagggc ggcgcgcagt tctacatctc gtgcgcccag ctcggcatca cggggcggcg      600
caacaccgac cgccgaaaca aggtcgcctt ccccggcgcc tactcgccca ccgacccggg      660
tatcctgatc aacatcaact ggcccatccc gacctcgtac accaaccccg gccccccggt      720
cttcacctgc taa                                                         733

<210> SEQ ID NO 23
<211> LENGTH: 328
<212> TYPE: PRT
<213> ORGANISM: Acremonium thermophilium

<400> SEQUENCE: 23

Met Lys Thr Ser Ser Ile Leu Thr Ala Ala Ser Ala Ala Thr Leu Ala
1               5                   10                  15

Ser Ala His Thr Ile Phe Val Gln Leu Gln Ser Gly Gly Thr Thr Tyr
            20                  25                  30

Pro Val Ser Tyr Ala Ile Arg Asp Pro Thr Tyr Asp Gly Pro Ile Thr
        35                  40                  45

Asp Val Thr Ser Asn Asp Leu Ala Cys Asn Gly Gly Pro Asn Pro Thr
    50                  55                  60
```

Thr Pro Ser Asp Lys Ile Ile Asn Val Ala Ala Gly Ser Thr Val Gln
65                  70                  75                  80

Ala Ile Trp Arg His Thr Leu Thr Ser Gly Pro Asp Asp Val Met Asp
                85                  90                  95

Ala Ser His Lys Gly Pro Thr Leu Ala Tyr Leu Lys Lys Val Asp Asn
            100                 105                 110

Ala Leu Thr Asp Ser Gly Ile Gly Gly Gly Trp Phe Lys Ile Gln Glu
        115                 120                 125

Asp Gly Tyr Asn Ser Gly Asn Trp Ala Thr Ser Lys Val Ile Asn Asn
    130                 135                 140

Gly Gly Phe Gln Asn Ile Thr Ile Pro Gln Cys Ile Ala Pro Gly Gln
145                 150                 155                 160

Tyr Leu Leu Arg Ala Glu Met Ile Ala Leu His Gly Ala Ser Ser Pro
                165                 170                 175

Gly Gly Ala Gln Leu Tyr Met Glu Cys Ala Gln Ile Asn Ile Thr Gly
            180                 185                 190

Gly Ser Gly Ser Val Thr Pro Thr Thr Tyr Ser Ile Pro Gly Ile Tyr
        195                 200                 205

Lys Glu Ser Trp Ser Asn Ser Arg Asn Phe Lys Ala Asn Asp Pro Gly
    210                 215                 220

Leu Leu Ile Asn Ile Tyr Ser Met Thr Pro Ser Ser Thr Tyr Val Ile
225                 230                 235                 240

Pro Gly Pro Asp Pro Phe Thr Cys Ser Ala Gly Gly Asn Asn Pro Pro
                245                 250                 255

Pro Ser Asn Pro Thr Thr Thr Leu Val Thr Val Thr Thr Lys Thr Thr
            260                 265                 270

Thr Thr Ser Ala Lys Thr Thr Thr Pro Pro Ser Asn Pro Thr Pro Pro
        275                 280                 285

Ser Gly Gly Cys Thr Ala Ala Gln Trp Ala Gln Cys Gly Gly Ile Gly
    290                 295                 300

Phe Thr Gly Cys Thr Thr Cys Ala Ser Gly Tyr Thr Cys Lys Thr Met
305                 310                 315                 320

Asn Asp Tyr Tyr Ser Gln Cys Gln
                325

<210> SEQ ID NO 24
<211> LENGTH: 246
<212> TYPE: PRT
<213> ORGANISM: Melanocarpus albomyces

<400> SEQUENCE: 24

Met Lys Leu Ser Leu Ala Ser Leu Leu Ala Ala Leu Ser Val Glu
1               5                   10                  15

Gly His Ala Ile Phe Gln Arg Leu Ser Val Asn Gly Gln Asp Gln Gly
            20                  25                  30

Glu Leu Asn Gly Leu Arg Ala Pro Asn Asn Asn Pro Val Gln Asp
        35                  40                  45

Val Asn Ser Gln Asn Met Ile Cys Gly Gln Pro Gly Tyr Thr Ser Gln
    50                  55                  60

Thr Val Ile Asp Val Gln Pro Gly Asp Arg Leu Gly Ala Trp Tyr Gln
65                  70                  75                  80

His Val Ile Gly Gly Pro Gln Phe Pro Gly Asp Pro Asp Asn Pro Ile
                85                  90                  95

Ala Ala Ser His Lys Gly Pro Ile Met Val Tyr Leu Ala Lys Val Asp

```
                  100                 105                 110
Asn Ala Ala Thr Ala Ser Leu Asn Gly Leu Lys Trp Phe Lys Ile Trp
            115                 120                 125

His Glu Gly Phe Asp Thr Ser Thr Arg Thr Trp Ala Val Asp Asn Leu
130                 135                 140

Ile Lys Asn Asp Gly Trp Val Tyr Phe Asp Leu Pro Gln Cys Ile Ala
145                 150                 155                 160

Pro Gly His Tyr Leu Met Arg Val Glu Leu Leu Ala Leu His Ser Ala
                165                 170                 175

Gly Met Pro Gly Gln Ala Gln Phe Tyr Thr Ser Cys Ala Gln Ile Asn
            180                 185                 190

Val Gly Gly Ser Gly Ser Phe Thr Pro Ser Gln Thr Val Ser Ile Pro
        195                 200                 205

Gly Val Tyr Ser Ala Asn Asp Pro Gly Ile Leu Ile Asn Ile Tyr Gly
    210                 215                 220

Ala Gln Gly Gln Pro Asp Asn Asn Gly Gln Pro Tyr Ser Ile Pro Gly
225                 230                 235                 240

Pro Glu Pro Ile Thr Cys
                245

<210> SEQ ID NO 25
<211> LENGTH: 225
<212> TYPE: PRT
<213> ORGANISM: Melanocarpus albomyces

<400> SEQUENCE: 25

Met Leu Pro Lys Ala Val Leu Leu Ala Ala Gly Leu Gly Ala Ser
1               5                   10                  15

Ala His Tyr Thr Leu Pro Arg Val Asn Ser Gly Ser Asp Trp Gln His
                20                  25                  30

Val Arg Arg Ala Asp Asn Trp Gln Asp Asn Gly Phe Val Gly Asp Val
            35                  40                  45

Asn Ser Pro Gln Ile Arg Cys Phe Gln Ser Ser His Ser Pro Ala Pro
    50                  55                  60

Glu Thr Leu Asn Val Thr Ala Gly Ser Ser Val Thr Tyr His Val Asn
65                  70                  75                  80

Pro Asn Ile Tyr His Pro Gly Pro Met Gln Phe Tyr Leu Ala Arg Val
                85                  90                  95

Pro Asp Gly Gln Asp Ile Asn Ser Trp Gln Gly Glu Gly Ala Val Trp
            100                 105                 110

Phe Lys Val Tyr His Glu Gln Pro Asn Phe Gly Gln Gln Leu Thr Trp
        115                 120                 125

Pro Ser Asn Gly Gln Ser Ser Phe Gln Val Pro Ile Pro Ser Cys Ile
    130                 135                 140

Arg Pro Gly Tyr Tyr Leu Leu Arg Ala Glu His Ile Ala Leu His Val
145                 150                 155                 160

Ala Gln Ser Gln Gly Gly Ala Gln Phe Tyr Ile Ser Cys Ala Gln Leu
                165                 170                 175

Gly Ile Thr Gly Gly Gly Asn Thr Asp Pro Pro Asn Lys Val Ala Phe
            180                 185                 190

Pro Gly Ala Tyr Ser Pro Thr Asp Pro Gly Ile Leu Ile Asn Ile Asn
        195                 200                 205
```

```
Trp Pro Ile Pro Thr Ser Tyr Thr Asn Pro Gly Pro Pro Val Phe Thr
    210                 215                 220
Cys
225
```

PROTEINS FOR THE TREATMENT OF CELLULOSIC MATERIAL

RELATED APPLICATION DATA

This application is a Utility Application which claims the benefit of Provisional Application No. 61/656,550 and filed Jun. 7, 2012 which is hereby incorporated by reference in its entirety.

The work leading to this invention has received funding from the European Community's Seventh Framework Programme FP7/2007-2013 under grant agreement n° 239341.

FIELD OF THE INVENTION

The present invention relates to novel polypeptides and enzyme preparations containing them, which enhance the efficiency of cellulosic degradation even at elevated temperatures. The invention also relates to polynucleotides, vectors and host cells comprising the polynucleotides as well as methods of producing the polypeptides. Furthermore, the present invention relates to a method for treating cellulosic material with the novel polypeptide or enzyme preparation, wherein the hydrolysis of cellulosic material is enhanced. The novel polypeptides are useful in treating cellulosic material. In addition the novel polypeptides may be used in detergent compositions, in machine dishwashing applications or for improving quality of animal feed.

BACKGROUND OF THE INVENTION

Limited resources of fossil fuels and increasing amounts of $CO_2$ released from them and causing the greenhouse phenomenon have raised a need for using biomass as a renewable and clean source of energy. Biomass resources can be broadly categorized as agricultural or forestry-based, including secondary sources derived from agro- and wood industries, waste sources and municipal solid wastes. One promising, alternative technology is the production of biofuels i.e. (bio)ethanol from lignocellulosic materials.

Most of the carbohydrates in plants are in the form of lignocellulose, which essentially consists of cellulose, hemicellulose, and lignin. Lignocellulose can be converted into bioethanol and other chemical products via fermentation following hydrolysis to fermentable sugars. In a conventional lignocellulose-to-ethanol process the lignocellulosic material is first pretreated either chemically or physically to make the cellulose fraction more accessible to hydrolysis. The cellulose fraction is then hydrolysed to obtain sugars that can be fermented by yeast or other fermentative organisms into ethanol and distilled to obtain pure ethanol. Lignin is obtained as a main co-product that may be used as a solid fuel.

One barrier of production of biofuels from cellulosic and lignocellulosic biomass is the robustness of the cell walls and the presence of sugar monomers in the form of inaccessible polymers that require a great amount of processing to make sugar monomers available to the micro-organisms that are typically used to produce alcohol by fermentation. Enzymatic hydrolysis is considered to be the most promising technology for converting cellulosic biomass into fermentable sugars. However, enzymatic hydrolysis is used only to a limited amount at industrial scale, and especially when using strongly lignified material such as wood or agricultural waste the technology is not satisfactory. The cost of the enzymatic step is one of the major economic factors of the process. Efforts have been made to improve the efficiency of the enzymatic hydrolysis of the cellulosic material (Badger 2002).

In addition to improving characteristics with respect to individual cellulolytic enzymes it would also be beneficial to improve the enzymatic degradation of cellulosic material by influencing on the activity of cellulases on lignocellulose. Optimization of the components in cellulase mixtures and supplementation of other synergistically acting enzymes would improve hydrolytic efficiency.

WO2005074647 and WO2011035027 disclose isolated polypeptides having cellulolytic enhancing activity and polynucleotides thereof from *Thielavia terrestris*. WO 2005074656 discloses an isolated polypeptide having cellulolytic enhancing activity and the polynucleotide thereof from *Thermoascus aurantiacus*. WO2007089290 discloses an isolated polypeptide having cellulolytic enhancing activity and the polynucleotide thereof from *Trichoderma reesei*. WO2008140749 relates to compositions and methods for degrading or converting a cellulose containing material with a cellulolytic enzyme composition comprising a *Trichoderma reesei* polypeptide having cellulolytic enhancing activity, and one or more components selected from the group consisting of a CEL7, CEL12 and CEL45 polypeptides having endoglucanase activity or cellobiohydrolase activity. WO2009085868 relates to isolated polypeptides having cellulolytic enhancing activity and polynucleotides thereof from *Myceliophthora thermophile*. WO2009033071 relates to fungal enzymes from *Chrysosporium lucknowense* (now reidentified as *Myceliophthora thermophile*; Visser et al. 2011) and methods for using the enzymes and compositions of such enzymes in a variety of other processes, including washing of clothing, detergent processes, biorefining, deinking and biobleaching of paper and pulp, and treatment of waste streams.

However, there is still a continuous need for new efficient methods of degrading cellulosic substrates, in particular lignocellulosic substrates, and for new cellulase enhancing factors, which can considerably improve the hydrolytic efficiency of cellulase mixtures and also reduce the required enzyme dosage. There is also a need for processes, which are versatile and allow the design of more flexible process configurations. Moreover, there is a need for processes which work not only at moderate temperatures but also at high temperatures, thus increasing the reaction rates and enabling the use of high biomass consistency leading to high sugar and ethanol concentrations. This approach may lead to significant savings in energy and investment costs. The high temperature also decreases the risk of contamination during hydrolysis. The present invention aims to meet at least part of these needs.

BRIEF DESCRIPTION OF THE INVENTION

It is an object of the present invention to provide novel polypeptides and enzyme preparations containing them, which enhance the efficiency of the cellulosic degradation even at elevated temperatures. Especially the object of the invention is to provide polypeptides to improve hydrolysis of lignocellulosic substrates in order to produce ethanol. Another object of the present invention is to provide a method for treating cellulosic material, wherein the hydrolysis of cellulosic material is enhanced and wherein versatile process configurations at variable conditions are possible.

The objects of the invention are achieved by novel polypeptides of GH family 61 obtained from *Acremonium thermophilium* or *Melanocarpus albomyces*.

The present invention provides a GH61 polypeptide comprising an amino acid sequence having at least 75% sequence identity to SEQ ID NO: 23, at least 78% sequence identity to SEQ ID NO: 24 or at least 79% sequence identity to SEQ ID NO: 25, or a fragment or variant thereof capable of enhancing hydrolysis of cellulosic material.

The present invention also relates to an isolated polynucleotide selected from the group consisting of:

a) a polynucleotide comprising the coding sequence as shown in SEQ ID NO: 20, 21 or 22;

b) a polynucleotide encoding a polypeptide of claim 1;

c) a polynucleotide encoding a fragment of a polypeptide encoded by a polynucleotide of a) or b), wherein said fragment is capable of enhancing hydrolysis of cellulosic material; and d) a polynucleotide comprising a nucleotide sequence which is degenerate to the nucleotide sequence of a polynucleotide sequence of a) or b);

or the complementary strand of such a polynucleotide.

The invention is also directed to a vector, which comprises said polynucleotide and a host cell comprising said vector. *Escherichia coli* strains having accession number DSM 25497, DSM 25495 and DSM 25499 are also included in the invention.

A further object of the invention is to provide a method of producing said GH61 polypeptide, the method comprising the steps of transforming a host cell with an expression vector encoding said polypeptide, and culturing said host cell under conditions enabling expression of said polypeptide, and optionally recovering and purifying said polypeptide.

Other objects of the invention are the enzyme preparations comprising at least one of the novel polypeptides and the use of said enzyme preparations and polypeptides for biomass processing, and in biofuel, starch, textile, detergent, pulp and paper, food, feed or beverage industry. In one aspect of the invention the polypeptides and enzyme preparation containing the polypeptide are used for cleaning the interior of a dishwashing machine. In another aspect the invention provides an animal feed comprising the novel polypeptide.

The invention also provides a method for treating cellulosic material with a GH61 polypeptide or an enzyme preparation comprising said polypeptide, wherein the method comprises reacting the fibrous/cellulosic material with said polypeptide or enzyme preparation comprising said polypeptide. In a preferred aspect of the invention the method of the invention comprises cleaning the interior of a dishwasher.

The present invention also provides a detergent composition comprising the GH61 polypeptide. The invention further relates to a method for improving fabric care properties or textile cleaning effect of a detergent composition, comprising adding a polypeptide of the invention to the detergent composition.

Specific embodiments of the invention are set forth in the dependent claims. Other objects, details and advantages of the present invention will become apparent from the following drawings, detailed description and examples.

The present inventors found that the novel GH61 polypeptides and methods of the invention offer considerable potential to increase the overall performance of cellulase enzyme mixtures and reduce the protein loading required to achieve effective hydrolysis of lignocellulosic substrates. The novel GH61 polypeptides are applicable in hydrolysing different cellulosic materials particularly in combination with enzymes used in hydrolysis of various cellulosic or lignocellulosic materials.

The present inventors also found that the novel GH61 polypeptides are very effective over a broad range of temperatures, and although they have high cellulolytic enhancing activity at standard hydrolysis temperatures, they are also very efficient at high temperatures. This makes them extremely well suited for varying cellulosic substrate hydrolysis processes carried out both at conventional temperatures and at elevated temperatures. In the conventional separate hydrolysis and fermentation process (SHF) the temperature of enzymatic hydrolysis is typically higher than that of fermentation. The use of thermostable enzymes in the hydrolysis offer potential benefits, such as higher reaction rates at elevated temperatures, reduction of enzyme load due to higher specific activity and stability of the enzymes, increased flexibility with respect to process configuration and decreased contamination risk. The general robustness of the thermostable enzymes compared to mesophilic ones also increases the recyclability of enzymes in the industrial process.

Furthermore, the inventors surprisingly found that novel GH61 polypeptides of the invention are effective in reducing fibrous/cellulosic fibres typically found in the filter of a dishwashing machine.

BRIEF DESCRIPTION OF THE DRAWINGS

In the following the invention will be described in greater detail by means of preferred embodiments with reference to the attached drawings.

Figure 1:
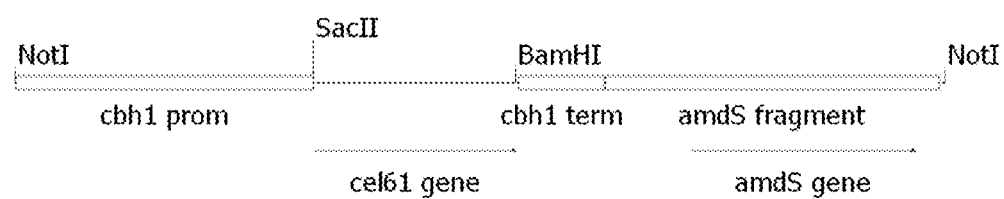
FIG. 1 schematically shows the cassette used for expressing the cel61 genes in *Trichoderma reesei*. The cel61 genes were under the control of *T. reesei* cbh1/cel7A promoter (cbh1 prom) and the termination of the transcription was ensured by using *T. reesei* cbh1/cel7A terminator sequence (cbh1 term). The amdS gene was included as a transformation marker.

(w/w) *T. reesei* cellulase mixture and 28% (w/w) of GH61 proteins At_GH61 or Ma_GH61A. Standard deviations are included in the graph.

SEQUENCE LISTING

SEQ ID NO:1 Sequence of a tryptic peptide 1669,824 from *Acremonium thermophilum* ALKO4245 At_GH61 protein.

SEQ ID NO:2 Sequence of a tryptic peptide 1763,938 from *Acremonium thermophilum* ALKO4245 At_GH61 protein.

SEQ ID NO:3 Sequence of a tryptic peptide 431.7752 from *Acremonium thermophilum* ALKO4245 At_GH61 protein.

SEQ ID NO:4 Sequence of a tryptic peptide 882.9711 from *Acremonium thermophilum* ALKO4245 At_GH61 protein.

SEQ ID NO:5 Sequence of a tryptic peptide 855.9166 from *Acremonium thermophilum* ALKO4245 At_GH61 protein.

SEQ ID NO:6 Sequence of an aminoterminal peptide #4349 from *Melanocarpus albomyces* ALKO4237 Ma_GH61B protein.

SEQ ID NO:7 Sequence of a tryptic peptide 2130,813 from *Melanocarpus albomyces* ALKO4237 Ma_GH61B protein.

SEQ ID NO:8 Sequence of a tryptic peptide 1283,527 from *Melanocarpus albomyces* ALKO4237 Ma_GH61B protein.

SEQ ID NO:9 Sequence of a tryptic peptide 2131,948 from *Melanocarpus albomyces* ALKO4237 Ma_GH61B protein.

SEQ ID NO:10 Sequence of a tryptic peptide 4466,106 from *Melanocarpus albomyces* ALKO4237 Ma_GH61B protein.

SEQ ID NO:11 The sequence of the oligonucleotide primer FIB54 derived from peptide SEQ ID NO:5.

SEQ ID NO:12 The sequence of the oligonucleotide primer FIB57 derived from peptide SEQ ID NO:1.

SEQ ID NO:13 The sequence of the oligonucleotide primer FIB99 derived from peptide SEQ ID NO:6.

SEQ ID NO:14 The sequence of the oligonucleotide primer FIB101 derived from peptide SEQ ID NO:9.

SEQ ID NO:15 The sequence of the oligonucleotide primer FIB35.

SEQ ID NO:16 The sequence of the oligonucleotide primer FIB38.

SEQ ID NO:17 The sequence of the PCR fragment obtained using the primers FIB54 (SEQ ID NO:11) and FIB57 (SEQ ID NO:12) and *Acremonium thermophilum* ALKO4245 genomic DNA as a template.

SEQ ID NO:18 The sequence of the PCR fragment obtained using the primers FIB99 (SEQ ID NO:13) and FIB101 (SEQ ID NO:14) and *Melanocarpus albomyces* ALKO4237 genomic DNA as a template.

SEQ ID NO:19 The sequence of the PCR fragment obtained using the primer FIB35 (SEQ ID NO:15) and FIB38 (SEQ ID NO:16) and *Melanocarpus albomyces* ALKO4237 genomic DNA as a template.

SEQ ID NO:20 The nucleotide sequence of the full-length *Acremonium thermophilum* ALKO4245 cel61 gene, At_cel61.

SEQ ID NO:21 The nucleotide sequence of the full-length *Melanocarpus albomyces* ALKO4237 cel61 gene, Ma_cel61a.

SEQ ID NO:22 The nucleotide sequence of the full-length *Melanocarpus albomyces* ALKO4237 cel61 gene, Ma_cel61b.

SEQ ID NO:23 The deduced amino acid sequence of the full-length *Acremonium thermophilum* ALKO4245 GH61 protein (At_GH61) including amino acids from Met1 to Gln328.

SEQ ID NO:24 The deduced amino acid sequence of the full-length *Melanocarpus albomyces* ALKO4237 GH61 protein (Ma_GH61A) including amino acids from Met1 to Cys246.

SEQ ID NO:25 The deduced amino acid sequence of the full-length *Melanocarpus albomyces* ALKO4237 GH61 protein (Ma_GH61B) including amino acids from Met1 to Cys225.

DEPOSITIONS

*Acremonium thermophilum* ALKO4245 was deposited at the Centraalbureau Voor Schimmelcultures at Upsalalaan 8, 3584 CT, Utrecht, the Netherlands on 20 Sep. 2004 and assigned accession number CBS 116240.

*Melanocarpus albomyces* ALKO4237 was deposited at the Centraalbureau Voor Schimmelcultures at Upsalalaan 8, 3584 CT, Utrecht, the Netherlands on 2 Mar. 2012 and assigned accession number CBS132099. ALKO4237 strain has also been previously deposited at the Centraalbureau Voor Schimmelcultures at Oosterstraat 1, 3740 AG BAARN, the Netherlands with accession number CBS 685.95 in 1995.

The *E. coli* strain RF9002 including the plasmid pALK2992 was deposited at the Deutsche Sammlung von Mikroorganismen und Zellkulturen GmbH (DSMZ), Inhoffenstrasse 7B, D-38124 Braunschweig, Germany on 15 Dec. 2011 and assigned accession number DSM25494.

The *E. coli* strain RF9091 including the plasmid pALK2993 was deposited at the Deutsche Sammlung von Mikroorganismen und Zellkulturen GmbH (DSMZ), Inhoffenstrasse 7B, D-38124 Braunschweig, Germany on 15 Dec. 2011 and assigned accession number DSM25495.

The *E. coli* strain RF9150 including the plasmid pALK3374 was deposited at the Deutsche Sammlung von Mikroorganismen und Zellkulturen GmbH (DSMZ), Inhoffenstrasse 7B, D-38124 Braunschweig, Germany on 15 Dec. 2011 and assigned accession number DSM25496.

The *E. coli* strain RF9319 including the plasmid pALK3375 was deposited at the Deutsche Sammlung von Mikroorganismen und Zellkulturen GmbH (DSMZ), Inhoffenstrasse 7B, D-38124 Braunschweig, Germany on 15 Dec. 2011 and assigned accession number DSM25497.

The *E. coli* strain RF9537 including the plasmid pALK3378 was deposited at the Deutsche Sammlung von Mikroorganismen und Zellkulturen GmbH (DSMZ), Inhoffenstrasse 7B, D-38124 Braunschweig, Germany on 15 Dec. 2011 and assigned accession number DSM25498.

The *E. coli* strain RF9696 including the plasmid pALK3379 was deposited at the Deutsche Sammlung von Mikroorganismen und Zellkulturen GmbH (DSMZ), Inhoffenstrasse 7B, D-38124 Braunschweig, Germany on 15 Dec. 2011 and assigned accession number DSM25499.

DETAILED DESCRIPTION OF THE INVENTION

Cellulose is the major structural component of higher plants. It provides plant cells with high tensile strength helping them to resist mechanical stress and osmotic pressure. Cellulose is a β-1,4-glucan composed of linear chains of glucose residues joined by β-1,4-glycosidic linkages. Cellobiose is the smallest repeating unit of cellulose. In cell walls cellulose is packed in variously oriented sheets, which are embedded in a matrix of hemicellulose and lignin. Hemicellulose is a heterogeneous group of carbohydrate polymers containing mainly different glucans, xylans and mannans. Hemicellulose consists of a linear backbone with β-1,4-linked residues substituted with short side chains usually containing acetyl, glucuronyl, arabinosyl and galactosyl. Hemicellulose can be chemically cross-linked to lignin. Lignin is a complex cross-linked polymer of variously substituted p-hydroxyphenylpropane units that provides strength to the cell wall to withstand mechanical stress, and it also protects cellulose from enzymatic hydrolysis.

"Cellulose" or "cellulosic material" as used herein, relates to any material comprising cellulose, hemicellulose and/or lignocellulose as a significant component. Cellulose is generally found, for example, in the stems, leaves, hulls, husks, and cobs of plants or leaves, branches, and wood of trees. The cellulosic material can be, but is not limited to, herbaceous material, agricultural residue, forestry residue, municipal solid waste, waste paper, and pulp and paper mill residue. Examples of cellulosic material include textile fibers derived e.g. from cotton, flax, hemp, jute and the man-made cellulosic fibers as modal, viscose and lyocel. Examples of cellulosic material also include fibrous or cellulosic type residues like soils found in a filter of automatic dishwashers.

"Lignocellulose" is a combination of cellulose and hemicellulose and lignin. It is physically hard, dense, and inaccessible and the most abundant biochemical material in the biosphere. "Lignocellulosic material" means any material comprising lignocellulose. Such materials are for example: hardwood and softwood chips, wood pulp, sawdust and forestry and wood industrial waste, agricultural biomass as cereal straws, sugar beet pulp, corn fibre, corn stover and cobs, sugar cane bagasse, stems, leaves, hulls, husks, and the like; waste products as municipal solid waste, newspaper and waste office paper, milling waste of e.g. grains; dedicated energy crops (e.g., willow, poplar, swithcgrass or reed canarygrass, and the like). Preferred examples are corn fibre, corn stover, switchgrass, cereal straw, sugarcane bagasse and wood derived materials.

Cellulosic material is degraded in nature by a number of various or ganisms including bacteria and fungi which produce enzymes capable of hydrolyzing carbohydrate polymers. Degradation usually requires different cellulases acting sequentially or simultaneously. Degradation of more complex cellulose containing substrates requires a broad range of various enzymes. For the degradation process the cellulosic material may be used as is or may be subjected to pretreatment, using conventional methods known in the art.

"Cellulolytic enzymes" or "cellulases" are enzymes having "cellulolytic activity", which means that they are capable of hydrolysing cellulosic substrates or derivatives thereof into smaller saccharides. Cellulolytic enzymes thus include both cellulases and hemicellulases. Hemicellulases, like xylanase and mannanase, are enzymes hydrolysing hemicellulose. Cellulases as used herein include (1) endoglucanases (EG, EC 3.2.1.4) which cut internal beta-1,4-glucosidic bonds; (2) exoglucanases or cellobiohydrolases (CBH, EC 3.2.1.176, EC 3.2.1.91) that cut the dissaccharide cellobiose from the reducing or non-reducing end of the crystalline cellulose polymer chain; (3) beta-1,4-glucosidases (BG, EC 3.2.1.21) which hydrolyze the cellobiose and other short cello-oligosaccharides to glucose. The CAZY (carbohydrate active enzymes) classification system collates glycosyl hydrolase (GH) enzymes into families according to sequence similarity, which have been shown to reflect shared structural features. In addition to this cellulases can be classified into various glycosyl hydrolase families according their primary sequence, supported by analysis of the three dimensional structure of some members of the family (Henrissat 1991, Henrissat and Bairoch 1993, 1996).

The GH61 polypeptides have cellulolytic enhancing activity, which means that they "enhance the hydrolysis of a cellulosic material" catalyzed by an enzyme having cellulolytic activity. In other words, saccharifying a cellulosic material with cellulolytic enzymes in the presence of a GH61 polypeptide increases the degradation of cellulosic material compared to the presence of only the cellulolytic enzymes. The cellulosic material can be any material containing cellulose. The term "Family 61 glycoside hydrolase" or "Family GH61" or "GH61 polypeptide" means a polypeptide falling into the glycoside hydrolase Family 61 (EC 3.2.1.4) according to Henrissat B., 1991, Biochem. J. 280: 309-316, and Henrissat B., and Bairoch A., 1996, Biochem. J. 316: 695-696. A GH61 protein is also referred to as a CEL61 protein.

GH61 proteins contain a core domain without a conventional glycoside hydrolase active site. In addition, GH61 proteins may contain a carbohydrate binding module/domain, also named as cellulose binding domain (CBM/CBD), which can be located either at the N- or C-terminus of the core domain. In general CBM mediates the binding of the protein to crystalline cellulose but has little or no effect on functional activity. These two domains are typically connected via a flexible and highly glycosylated linker region.

The present invention is based on studies, which attempted to find novel GH61 family polypeptides which would enhance hydrolysis efficiency of cellulosic substrates and which could be used for versatile applications even at elevated temperatures. Three novel GH 61 family polypeptides referred to as At_GH61, Ma_GH61A and Ma_GH61B were obtained (Table 1).

TABLE 1

The GH61 genes and polypeptides of the invention

| Gene | nucleic acid SEQ ID NO: | Protein | No of aas | amino acid SEQ ID NO: |
|---|---|---|---|---|
| At_cel61 | 20 | At_GH61 | 328 | 23 |
| Ma_cel61a | 21 | Ma_GH61A | 246 | 24 |
| Ma_cel61b | 22 | Ma_GH61B | 225 | 25 |

The novel GH61 polypeptides according to the present invention are obtainable from *Acremonium thermophilum* or *Melanocarpus albomyces*. Preferably the polypeptides are obtainable from *A. thermophilium* strain having the characteristics of strain ALKO4245 deposited as CBS 116240 or *M. albomyces* strain having the characteristics of strain ALKO4237 deposited as CBS 132099. "Obtainable from" means that they can be obtained from said species, but it does not exclude the possibility of obtaining them from other sources. In other words they may originate from any organism including plants. Preferably they originate from microorganisms e.g. bacteria or fungi. The bacteria may be for example from a genus selected from *Bacillus, Azospirillum* and *Streptomyces*. More preferably the enzyme originates from fungi (including filamentous fungi and yeasts), for example from a genus selected from the group consisting of *Thermoascus, Acremonium, Chaetomium, Achaetomium, Thielavia, Aspergillus, Botrytis, Chrysosporium, Collybia,*

*Fomes, Fusarium, Humicola, Hypocrea, Lentinus, Melanocarpus, Myceliophthora, Myriococcum, Neurospora, Penicillium, Phanerochaete, Phlebia, Pleurotus, Podospora, Polyporus, Rhizoctonia, Scytalidium, Pycnoporus, Talaromyces, Trametes* and *Trichoderma*.

The novel GH61 polypeptides of the invention preferably comprise an amino acid sequence having at least 75% sequence identity to SEQ ID NO: 23, at least 78% sequence identity to SEQ ID NO: 24 or at least 79% sequence identity to SEQ ID NO: 25, or a fragment or variant thereof capable of enhancing hydrolysis of cellulosic material. According to one embodiment of the invention, the polypeptide has at least 80, 85, 90, 95, 98 or 99% identity to SEQ ID NO: 23, SEQ ID NO: 24 or SEQ ID NO: 25 or to a fragment thereof capable of enhancing hydrolysis of cellulosic material. According to another embodiment of the invention, the polypeptide has at least 90%, preferably 95%, and most preferably at least 98% identity to SEQ ID NO: 23, SEQ ID NO: 24 or SEQ ID NO: 25 or to a fragment thereof capable of enhancing hydrolysis of cellulosic material.

By the term "identity" is here meant the global identity between two amino acid sequences compared to each other from the first amino acid encoded by the corresponding gene to the last amino acid. The identity of the full-length sequences is measured by using EMBOSS Needle Needleman-Wunsch global alignment program at EBI (European Bioinformatics Institute) http://www.ebi.ac.uk/Tools/psa/emboss_needle/with the following parameters: BLOSUM50, Gap open 10.0, Gap extend 0.5. The algorithm is described in Needleman and Wunsch (1970). The man skilled in the art is aware of the fact that results using Needleman-Wunsch algorithm are comparable only when aligning corresponding domains of the sequence and using the same parameters in each comparison. Consequently comparison of e.g. cellulase sequences including CBM or signal sequences with sequences lacking those elements cannot be done.

By the term "fragment enhancing hydrolysis of cellulosic material" is meant any fragment of a defined sequence that has capability to enhance hydrolysis of cellulosic material catalyzed by an enzyme having cellulolytic activity. In other words a fragment enhancing hydrolysis of cellulosic material may be the mature protein part of the defined sequence, or it may be only a fragment of the mature protein part, provided that it still has capability to enhance hydrolysis of cellulosic material. For purposes of the present invention, cellulolytic enhancing activity is determined by measuring the increase of the total glucose concentration from the hydrolysis of a cellulosic material by a cellulolytic enzyme mixture containing the GH61 polypeptide compared to equal protein loading of the cellulolytic enzyme mixture without the GH61 polypeptide.

The novel polypeptides may also be variants of said polypeptides. A "variant" may be a polypeptide that occurs naturally e.g. as an allelic variant within the same strain, species or genus, or it may have been generated by mutagenesis. It may comprise amino acid substitutions, deletions or insertions, but it still functions in a substantially similar manner to the polypeptides defined above i.e. it comprises a fragment enhancing hydrolysis of cellulosic material.

The GH61 are usually produced in the cell as prepolypeptides comprising a signal sequence that is cleaved off during secretion of the protein. They may also be further processed during secretion both at the N-terminal and/or C-terminal end to give a mature, enzymatically active protein. "A polypeptide enhancing hydrolysis of cellulosic material" thus denotes that the polypeptide may be either in immature or mature form, preferably it is in mature form, i.e. the processing has taken place. In addition, the "mature form" means an enzyme which has been cleaved from its carrier protein in fusion constructions.

The polypeptides of the present invention are preferably recombinant proteins, which may be produced in a generally known manner. A polynucleotide fragment of the GH61 gene is isolated, the gene is inserted under a strong promoter into an expression vector, the vector is transformed into suitable host cells and the host cells are cultivated under conditions provoking production of the enzyme. Methods for protein production by recombinant technology in different host systems are well known in the art (Sambrook et al., 2001; Coen, 2001; Gellissen, 2005). Preferably the polypeptides are produced as extracellular proteins that are secreted into the culture medium, from which they can easily be recovered and isolated.

The recombinant polypeptide may be a fused polypeptide in which another polypeptide is fused at the N-terminus or the C-terminus of the polypeptide of the present invention. Techniques for producing fusion polypeptides are known in the art, and include ligating the coding sequences encoding the polypeptides so that they are in frame and that expression of the fused polypeptide is under control of the same promoter and terminator.

The GH61 polypeptides of the invention may be used with a signal sequence included or without a signal sequence and/or CBM or the signal sequence and/or CBM may derive from different enzymes of the above mentioned microorganisms or different microorganism or be synthetically or recombinantly incorporated to the core domain of the above proteins.

The present invention relates to novel polynucleotides which comprise a nucleotide sequence of SEQ ID NO: 20, 21, or 22, or a sequence encoding a novel polypeptide as defined above, including complementary strands thereof. "Polynucleotide" as used herein refers to both RNA and DNA, and it may be single stranded or double stranded. Further the polynucleotide may be degenerate as a result of the genetic code to any one of the sequences as defined above. This means that different codons may code for the same amino acid.

The polynucleotide may also be a fragment of said polynucleotides comprising at least 24 nucleotides, e.g. at least 25, 30, 40 or 50 nucleotides. According to one embodiment of the invention the polynucleotide has a sequence set forth as SEQ ID NO 11, 12, 13, 14, 15 or 16.

Within the context of the invention is a GH61 polypeptide, which is encoded by a nucleic acid molecule or polynucleotide sequence hybridizing under stringent conditions to a polynucleotide sequence or a subsequence thereof included in SEQ ID NO: 20, 21, or 22. Hybridization performed at "high stringency" conditions may be hybridization at a temperature, which is 20-25° C. below the calculated melting temperature (Tm) of a perfect hybrid, the Tm calculated according to Bolton and McCarthy (1962) and posthybridization washes in low salt concentration. Usually prehybridization and hybridization are performed at least at 65° C. in 6×SSC (or 6×SSPE), 5×Denhardt's reagent, 0.5% (w/v) SDS, 100 µg/ml denatured, fragmented salmon sperm DNA. Addition of 50% formamide lowers the prehybridization and hybridization temperatures to 42° C. High stringency washes are performed in low salt concentration, e.g. in 2×SSC-0.1% SDS (w/v) at RT, and finally in 0.1×SSC-0.1% SDS (w/v) at least at 65° C., e.g. at 68° C.

According to another embodiment of the invention, the polynucleotide comprises a gene similar to that included in a microorganism having accession number DSM 25497, DSM 25495 or DSM 25499.

The present invention relates to a recombinant expression "vector" comprising a polynucleotide encoding the GH61 polypeptide as characterized above, operably linked to regulatory sequences, which are capable of directing the expression of a gene encoding said GH61 polypeptide in a suitable host. Said regulatory sequences may be homologous or heterologous to the production organism or they may originate from the organism, from which the gene encoding the GH61 polypeptide of the invention is isolated. The expression vector may further comprise marker genes for selection of the transformant strains or the selection marker may be introduced to the host in another vector construct by co-transformation.

Still the present invention relates to a production "host", which can be any homologous or heterologous organism capable of expressing the desired polypeptide. Preferably the host is a microbial cell, more preferably a fungus. Most preferably the host is a filamentous fungus. Preferred hosts for producing the polypeptides of the invention are in particular strains from the genus *Trichoderma* or *Aspergillus*. Preferably the recombinant host is modified to express and secrete cellulolytic enzymes or polypeptides of the invention as its main activity or one of its main activities. This can be done by deleting genes encoding major homologous secreted enzymes e.g. the four major cellulases of *Trichoderma* and by integrating heterologous genes to a locus with high expression and production levels.

The present invention relates also to a method for producing a GH61 polypeptide of the invention, said method comprising the steps of transforming a host cell with an expression vector encoding said polypeptide, and culturing said host cell under conditions enabling expression of said polypeptide, and optionally recovering and purifying said polypeptide. The production medium may be a medium suitable for growing the host organism and containing inducers for efficient expression.

The polypeptides of the present invention may be isolated, which in the present context may simply mean that the cells and cell debris have been removed from the culture medium containing the polypeptide. Conveniently the polypeptides are isolated e.g. by adding anionic and/or cationic polymers (flocculants) to the spent culture medium to enhance precipitation of cells and cell debris. The medium is then filtrated using an inorganic filtering agent and a filter to remove the precipitants formed. After this the filtrate is further processed using a semi-permeable membrane to remove excess of salts, sugars and metabolic products. The polypeptides can also be purified or concentrated by crystallization.

The novel GH61 polypeptides which are obtainable by the method of the present invention may be components of an enzyme preparation. The term "enzyme preparation" denotes to a composition comprising at least one of the novel polypeptides described herein. The polypeptide in the enzyme preparation may be a recombinant GH61 protein comprising an amino acid sequence having at least 75% sequence identity to SEQ ID NO: 23, at least 78% sequence identity to SEQ ID NO: 24 or at least 79% sequence identity to SEQ ID NO: 25, or a fragment or variant thereof capable of enhancing hydrolysis of cellulosic material. According to one embodiment of the invention the enzyme preparation comprises a polypeptide having at least 80, 85, 90, 95, 98 or 99% identity to SEQ ID NO: 23, SEQ ID NO: 24 or SEQ ID NO: 25.

The enzyme preparation may further comprise at least one enzyme selected from a group of cellobiohydrolase, endo-glucanase, beta-glucosidase, beta-glucanase, xyloglucanase, xylanase, beta-xylosidase, cellobiose dehydrogenase, mannanase, beta-mannosidase, $\alpha$-glucuronidase, acetyl xylan esterase, $\alpha$-arabinofuranosidase, $\alpha$-galactosidase, pectinase, involving endo- and exo-$\alpha$-L-arabinases, endo- and exo-galactoronase, endopectinlyase, pectate lyase, and pectinesterase, phenol esterase, ligninase involving lignin peroxidase, manganese-dependent peroxidase, $H_2O_2$-generating enzyme, laminarinase, chitosanase, ferulic acid esterase and laccase with or without mediators. The enzyme preparation may contain any combination of these enzymes and GH61 polypeptide of the invention, but the enzymes are not limited to those described herein. They can for example also be commercially available enzyme preparations.

Preferably in addition to the GH61 polypeptide the enzyme preparation comprises at least cellobiohydrolase, endoglucanase, beta-glucosidase and optionally xylanase. Different mixtures of GH61 polypeptides and cellulolytic enzymes may be used to suit different process conditions.

In addition to the GH61 proteins, the enzyme preparation of the invention may contain additives, such as mediators, stabilizers, buffers, preservatives, surfactants and/or culture medium components. Preferred additives are such, which are commonly used in the enzyme preparations intended for a particular application. The enzyme preparations of the invention may also contain metal and/or redox-active cofactors.

The enzyme preparation may be in the form of liquid, powder or granulate. It may be a filtrate containing one or more cellulolytic enzymes. Preferably the enzyme preparation is a spent culture medium. "Spent culture medium" refers to the culture medium of the host comprising the produced enzymes/polypeptides. Preferably the host cells are separated from the said medium after the production. The enzyme preparation or composition may also be a "whole culture broth" obtained, optionally after inactivating the production host(s) or microorganism(s) without any biomass separation, down-stream processing or purification of the desired cellulolytic enzyme(s). In the consolidated bioprocess the enzyme composition or at least some of the enzymes of the enzyme composition may be produced by the fermentative microorganism.

The enzyme preparation may contain the polypeptides in at least partially purified and isolated form. It may even essentially consist of the desired polypeptide. The culture medium with or without host cells may be utilized as an enzyme preparation as such without further purification, because the GH61 proteins can be secreted into the culture medium, and they display activity in the ambient conditions of the spent culture medium.

The present invention provides a method for treating cellulosic material, wherein the cellulosic material is reacted with an effective amount of the GH61 polypeptide or the enzyme preparation comprising said GH61 polypeptide in the presence of cellulolytic enzymes under suitable conditions, such as appropriate pH and temperature, and the reaction is allowed to continue for a time sufficient for the enzymatic reaction to take place. The GH61 polypeptides enhance the activity of cellulolytic enzymes, either in the acid, neutral, or alkaline pH-range.

The GH61 polypeptides of the invention are capable of enhancing hydrolysis of cellulosic material at moderate to elevated temperatures. The term "moderate temperature" or "conventional temperature" in context of the present invention means temperatures commonly used in cellulose hydrolysis and corresponding to the optimal temperatures or thermal stabilities of the enzymes used in such processes. Thus, the terms refer to temperature ranges from about 30° C. to 45° C. The term "elevated temperature" or "high temperature" refers to temperature ranges from about 45° C. to 70° C. Enzymes active or stable at such elevated temperature ranges are also called "thermostable" or "thermophilic" enzymes. The GH61 polypeptides of the invention are used preferably at temperatures between about 35° C. and 60° C. More preferably they are used at temperatures between 37° C. and 55° C., most preferably at temperatures between 45° C. and 55° C. In addition, these temperatures are also applicable to the use of GH61 polypeptides of the invention for improving fabric care properties or textile cleaning effect of a detergent composition and further in biofinishing and biostoning.

The GH61 polypeptides are especially suitable for producing fermentable sugars from lignocellulosic material. The fermentable sugars may then be fermented by yeast into ethanol, and used as fuel. They can also be used as intermediates or raw materials for the production of various chemicals or building blocks for the processes of chemical industry, e.g. in so called biorefinery. Any method known in the art comprising pretreatment, enzymatic hydrolysis, fermentation, or a combination thereof, can be used in the context of the present invention. Current pretreatments include mechanical, chemical or thermal processes and combinations thereof. The material may for example be pretreated by steam explosion or acid hydrolysis.

According to one embodiment of the present invention the method of treating cellulosic material comprises cleaning the interior of a dishwasher by contacting at least part of the interior of the dishwasher with the GH61 polypeptide of the invention or the enzyme preparation comprising said GH61 polypeptide. The enzyme preparation of the invention may be placed directly into the interior of the machine or alternatively into a dispensing draw or cup of the machine or to areas in the interior of the dishwasher, which require removal of fibrous soils (e.g. the filter). Useful methods for cleaning dishwasher machine are described e.g. in WO2011161459. The enzyme preparation may also be specifically applied to those areas of a dishwasher machine, where fibrous/cellulosic soil is deposited. The method may be applicable manually whilst the dishwasher is not being operated or whilst the dishwasher is undergoing a loaded or unloaded washing and/or rinsing cycle. Moreover, the GH61 polypeptides of the present invention may be used at all wash temperatures of a dishwashing system, even at temperatures greater than 55° C.

The GH61 polypeptides may be used to degrade tough fibrous/cellulosic soils which may otherwise be difficult to remove from the interior of the dishwashing machine such as from the filter. Soils which can be broken down by the GH61 polypeptide or the enzyme preparation containing said polypeptide include cereals, fruits and vegetables. Some specific examples include apple and orange peels and wheat fiber.

The novel GH61 polypeptides, enzyme preparations and the methods of the invention may be applied in any process involving cellulolytic enzymes, such as biomass processing, and in biofuel, starch, textile, detergent, pulp and paper, food, feed or beverage industry. They may be used for treating any cellulosic material, such as textile material, plants used in animal feed, or wood-derived mechanical or chemical pulp or secondary fiber. They may also be added into detergents and other media used for such applications. The GH61 polypeptides can also be added to wastewater to reduce the amount of solids such as sludge.

The GH61 polypeptides of the present invention may be used as a detergent additive suitable for laundry detergent and dish wash compositions, including automatic dish washing compositions. A detergent means a substance or material intended to assist cleaning or having cleaning properties. Preferably the GH61 polypeptides of the present invention may be used in an automatic dishwasher cleaning composition that works well at all wash temperatures of a dishwashing system, even at temperatures greater than 55° C.

The present invention relates to a detergent composition comprising a GH61 polypeptide or an enzyme preparation of the invention and optionally one or more surfactants. Preferably a detergent composition contains an enzyme preparation of the invention comprising at least one GH61 polypeptide and other enzymes selected from the group of protease, amylase, cellulase, lipase, xylanase, mannanase, cutinase, pectinase or oxidase with or without a mediator as well as suitable additives selected from the group of stabilizers, buffers, surfactants, bleaching agents, mediators, anti-corrosion agents, builders, antiredeposition agents, optical brighteners, dyes, pigments, caustics, abrasives and preservatives, etc. Cellylolytic enzymes may be used in detergent compositions, for example, for the purpose of improving fabric care properties by antipilling, antigraying, color clarification and softening, and to improve textile cleaning effect, for instance soil removal.

The enzyme preparations of the invention may contain a surfactant which can be anionic, non-ionic, cationic, amphoteric or a mixture of these types, especially when used as a detergent composition, Useful detergent compositions are described e.g. in WO 94/07998, U.S. Pat. No. 5,443,750 and U.S. Pat. No. 3,664,961.

The present invention also relates a method for enhancing the cleaning ability of a detergent composition for a dishwasher, comprising adding a polypeptide or enzyme preparation of the invention to the detergent composition. Furthermore, the invention relates to a method for improving fabric care properties or textile cleaning effect of a detergent composition, comprising adding a polypeptide or enzyme preparation of the invention to the detergent composition.

The enzyme preparations of the invention are useful in the treatment of textile materials, such as fabrics and garments. The textile material may be manufactured of natural cellulose containing fibers or man-made cellulose containing fibers or mixtures thereof, or a blend of synthetic fibers and cellulose containing fibers. The enzyme preparations of this invention are especially useful in biofinishing. "Biofinishing" refers to the use of enzymes in a controlled hydrolysis of cellulosic fibers in order to modify the fabric or yarn surface in a manner that prevents permanently pilling, improves fabric handle like softness and smoothness, clears the surface structure by reducing fuzzing, which results in clarification of colors, improves the drapability of the fabric, improves moisture absorbability and which may improve also the dyeability. Additional uses further include the use in biostoning of denim. "Biostoning" refers to the enzymatic denim finishing processes in which cellulases have replaced or are being used together with pumice stones to give the fabric its desired "worn" look. Controlled enzyme treatments result in less damage to the garments and machines and eliminate the need for disposal of stones.

The invention is described by the following non-limiting examples. It will be obvious to a person skilled in the art that, as the technology advances, the inventive concept can be implemented in various ways. The invention and its embodiments are not limited to the examples described but may vary within the scope of the invention.

EXAMPLES

Example 1

Purification of GH61 Proteins from *Melanocarpus albomyces* ALKO4237 and *Acremonium thermophilum* ALKO4245

Fungal strains *Acremonium thermophilum* ALKO4245 (CBS 116240) and *Melanocarpus albomyces* ALKO4237 (CBS 132099) were grown, maintained and sporulated on Potato Dextrose (PD) agar (Difco) at +4° C. The PD slants of the ALKO4237 and ALKO4245 strains were inoculated into a complex culture medium which contained: 18 g/l Solka-Floc® cellulose (International Fiber Europe N.V., Belgium), 18 g/l Distiller's spent grain, 9 g/l Locust bean gum, 9 g/l Oats spelt xylan, 4.5 g/l Soybean meal, 3 g/l Wheat bran, 2 g/l $CaCO_3$, 4.5 g/l $(NH_4)HPO_4$, 1.5 g/l $KH_2PO_4$, 1.5 g/l $MgSO_4 \times H_2O$, 0.9 g/l KNO3, 0.5 g/l NaCl and trace elements $MnSO_4$, $ZnSO_4$, $CoCl_2$ and $FeSO_4$. The pH of the medium was adjusted before sterilization with KOH to 6.5-7.5 and the medium was autoclaved for 15 minutes at 121° C. The microbes were cultivated on a shaker (250 rpm) at 42° C. for 7-9 days. Cells and solids were removed from the spent culture medium by centrifugation. The spent culture supernatants were analyzed on sodium dodecyl sulfate polyacrylamide gel electrophoresis (SDS-PAGE).

The culture supernatants were subjected to purification steps to separate proteins to fractions. Culture supernatant of *Acremonium thermophilum* ALKO4245 was subjected to cellulose-affinity purification step to identify proteins that are capable to bind cellulose. One gram of cellulose powder AlphaCel™ BH300 (International Fiber Europe N.V., Belgium) was suspended in 40 ml Milli-Q water. The cellulose suspensions was agitated for 5 min and centrifuged 2000×g for 5 min. The pellet was suspended in pure Milli-Q water and washing steps were repeated 3 times. Cellulose was suspended in 3 ml of Milli-Q water and 0.5 ml of cellulose suspension was added to a mixture of 10 ml of spent culture supernatant and 10 ml of 20 mM Hepes, 75 mM NaCl, pH 7. The sample was agitated on ice for 30 min and centrifuged for 2000×g for 5 min. The pellet was washed 3 times with 40 ml of cold 20 mM Hepes, 75 mM NaCl, pH 7-buffer. Proteins were eluted from cellulose by incubating the sample for 10 min at 60° C. with 200 µl of SDS-PAGE sample buffer. Eluted proteins were analyzed on SDS-PAGE gel and protein bands were identified by amino acid sequencing (Example 2).

A 410 ml batch of *Melanocarpus albomyces* ALKO4237 culture supernatant was filtered through a 0.44 µm filter (MILLEX HV Millipore, Mass., USA). 43.6 g of solid ammonium sulfate was dissolved into the sample and incubated on ice for 30 min. Precipitated proteins were collected by centrifugation 15 min, 10000×g at +4° C. The pellet was dissolved into 10 ml of 20 mM Hepes, pH 7.5. The sample was filtered through a 0.44 µm filter (MILLEX HV Millipore, Mass., USA) and applied to a 5 mL Q Sepharose FF column (GE Healthcare, UK) equilibrated with 20 mM Hepes, pH 7.5. Flow through fraction was collected and concentrated to 2 ml using Macrosep 10K centrifugal device (PALL Life Sciences, NY, USA). The sample was further fractionated using Superdex 26/60 75 pg gel-filtration column equilibrated with 20 mM MES, 100 mM NaCl, pH 6.5. Eluted fractions were analyzed on SDS-PAGE gel and protein bands with expected sizes according to calculations basing on published GH61 sequences were identified by amino acid sequencing (Example 2).

Example 2

Amino Acid Sequencing of the Purified Proteins from *Melanocarpus albomyces* ALKO4237 and *Acremonium thermophilum* ALKO4245

For determination of internal sequences, the Coomassie Brilliant Blue stained band was cut out of the polyacrylamide gel and "in-gel" digested essentially as described by Shevchenko et al. (1996). Proteins were reduced with dithiothreitol and alkylated with iodoacetamide before digestion with trypsin (Sequencing Grade Modified Trypsin, V5111, Promega, Wis., USA) and mass determination.

Electrospray ionization quadrupole time-of-flight tandem mass spectra for de novo sequencing were generated using a Q-TOF instrument (Micromass, Manchester, UK) connected to an Ultimate nano liquid chromatograph (LC-Packings, The Netherlands) essentially as described previously (Poutanen et al., 2001) but using a 150 µm×1.0 mm trapping column (3 µm, 120 Å, #222403, SGE Ltd, UK) for peptide preconcentration.

For N-terminal sequence analysis SDS-PAGE separated proteins were transferred by electroblotting into a polyvinylidine difluororide membrane (ProBlott; Perkin Elmer Applied Biosystems Division, CA, USA) After being stained with Coomassie brilliant blue, the protein bands of interest were removed and subjected to N-terminal sequence analysis by Edman degradation on a Procise 494A protein sequencer (Perkin Elmer Applied Biosystems Division, CA, USA).

The peptide sequences determined from the purified proteins were analyzed. Internal peptides from a 46 kDa purified protein from *Acremonium thermophilum* ALKO4245 showed similarity to a published unnamed protein product from *Sordaria macrospora* with Accession number CBI52679. Protein CBI52679 is similar to proteins of the Glycoside Hydrolase family 61. Thus the 46 kDa protein from *Acremonium thermophilum* is named At_GH61. N-terminal and internal peptides from a 22 kDa purified protein from *Melanocarpus albomyces* ALKO4237 showed similarity to a published hypothetical protein from *Chaetomium globosum* with Accession number XP_001225931. The hypothetical protein XP_001225931 is similar to family GH61 proteins. The 22 kDa protein from *Melanocarpus albomyces* is thus named Ma_GH61B. The internal and N-terminal peptide sequences obtained from proteins At_GH61 (SEQ ID NOs: 1-5) and Ma_GH61B (SEQ ID NOs: 6-10) are shown in Table 2.

TABLE 2

Internal peptide sequences determined from the purified proteins At_GH61 from *Acremonium thermophilum* and Ma_GH61B from *Melanocarpus albomyces*

| Protein | Peptide | Sequence | SEQ ID NO: | Comment |
|---|---|---|---|---|
| At_GH61 | 1669,824 | EDGYNSGNWATSK | 1 | de novo |
| | 1763,938 | DNALTDSGLGNWFK | 2 | de novo; L can be L or I |
| | 431.7752 | KGPTLAYLKK | 3 | mass map |
| | 882.9711 | KKVDNALTDSGIGGGWFKI | 4 | mass map |
| | 855.9166 | RHTLTSGPDDVMDASHKG | 5 | mass map |
| Ma_GH61B | #4349 | HYTLPRVNSGSDWQHVRRADNWQ | 6 | N-terminus |
| | 2130,813 | NGFVGDVNSPQLR | 7 | de novo; L can be L or I |
| | 1283,527 | VNSGSDWQHVR | 8 | de novo |
| | 2131,948 | NSWQADGAVWFK | 9 | de novo |
| | 4466,106 | PSDGQSSFQVP | 10 | de novo |

Example 3

Cloning of the cel61 Genes from *Acremonium thermophilum* ALKO4245 and *Melanocarpus albomyces* ALKO4237

Standard molecular biology methods were used in the isolation and enzyme treatments of DNA (e.g. isolation of plasmid DNA, digestion of DNA to produce DNA fragments), in *E. coli* transformations, sequencing etc. The basic methods used were either as described by the enzyme, reagent or kit manufacturer or as described in the standard molecular biology handbooks, e.g. Sambrook and Russell (2001). Isolation of genomic DNA was performed as described in detail by Raeder and Broda (1985).

Degenerate oligonucleotides were planned basing on the amino acid sequences of the peptides obtained from the purified At_GH61 and Ma_GH61B proteins (Table 2). The degenerate oligos were used to synthesize probes for the genes encoding the proteins. Sequences of the degenerate oligos used as primers are shown in Table 3 (SEQ ID NOs: 11-14).

Primer combination of FIB54 and FIB57 (SEQ ID NOs: 11-12) produced a 349 bp PCR product with *Acremonium thermophilum* ALKO4245 genomic DNA as template in PCR conditions containing 1× Phusion GC buffer, 0.25 mM dNTPs, 1 µM of primers FIB54 and FIB57 (Table 3), 1-2 units of Phusion DNA polymerase (Finnzymes, Finland) and 0.5-3 µg of the ALKO4245 genomic DNA per 100 µl reaction volume. The conditions for the PCR reactions were the following: 1 min initial denaturation at 98° C., followed by 29 cycles of 10 sec at 98° C., 30 sec annealing at 52° C. (±8° C. gradient), 30 sec extension at 72° C. and a final extension at 72° C. for 5 min. The obtained PCR product had the expected size according to calculations basing on published cel61 sequences. The PCR product was isolated and purified from the PCR reaction mixture and cloned to pCR®4Blunt-TOPO®-vector according to the manufacturer's instructions (Invitrogen, USA). The insert was characterized by sequencing.

Primer combination of FIB99 and FIB101 (SEQ ID NOs: 13-14) produced a 239 bp PCR product with *Melanocarpus albomyces* ALKO4237 genomic DNA as template in PCR conditions containing 10 mM Tris-HCl, pH 8.8, 50 mM KCl, 0.1% Triton X-100, 1.5 mM MgCl$_2$, 0.2 mM dNTPs, 1 µM of primers FIB99 and FIB101 (Table 2), 2 units of Dynazyme II DNA polymerase (Finnzymes, Finland) and 0.5-3 µg of the ALKO4237 genomic DNA per 100 µl reaction volume (optional 5% DMSO). The conditions for the PCR reactions were the following: 5 min initial denaturation at 95° C., followed by 31 cycles of 1 min at 95° C., 30 sec annealing at 50° C. (±8° C. gradient), 1 min extension at 72° C. and a final extension at 72° C. for 5 min. The obtained PCR product had the expected size according to calculations basing on published cel61 sequences. The PCR product was isolated and purified from the PCR reaction mixture and cloned to pCR®4-TOPO-TA®-vector according to the

TABLE 3

The oligonucleotides used as PCR primers to amplify probes for cel61 genes from *Acremonium thermophilum* ALKO4245 and *Melanocarpus albomyces* ALKO4237

| Template, genomic DNA from | Peptide[a] | Oligonucleotide | Length (bp) | Sequence[b] | SEQ ID NO: |
|---|---|---|---|---|---|
| ALKO4245 | 855.9166 | FIB54 | 19 | GGNCCNGAYGAYGTNATGG (s) | 11 |
| | 1669,824 | FIB57 | 15 | NGTNGCCCARTTNCC (as) | 12 |
| ALKO4237 | #4349 | FIB99 | 17 | GNGCNGAYAAYTGGCAR (s) | 13 |
| | 2131,948 | FIB101 | 24 | YTTRAACCANACNGCNCCRTCNGC (as) | 14 |
| ALKO4237 | | FIB35 | 18 | ACNGAYATHAAYGGNTGG (s) | 15 |
| | | FIB38 | 23 | GGNARRTTNGGDATNCCRTCRTT | 16 |

[a]The peptide sequences are included in Table 1.
[b]N = A or G or T or C, Y = T or C, R = A or G, H = A or T or C, D = G or A or T; "s" in the parenthesis = sense strand, "as" in the parenthesis = anti-sense strand.

manufacturer's instructions (Invitrogen, USA). The insert was characterized by sequencing.

Primer combination of FIB35 and FIB38 (SEQ ID NOs: 15-16) produced a 860 bp PCR product with *Melanocarpus albomyces* ALKO4237 genomic DNA as template in PCR conditions containing 1× Phusion GC buffer, 5% DMSO, 0.25 mM dNTPs, 1 µM of primers FIB35 and FIB38 (Table 2), 1-2 units of Phusion DNA polymerase (Finnzymes, Finland) and 0.5-3 µg of the ALKO4237 genomic DNA per 100 µl reaction volume. The conditions for the PCR reactions were the following: 1 min initial denaturation at 98° C., followed by 29 cycles of 10 sec at 98° C., 30 sec annealing at 48° C. (±8° C. gradient), 30 sec extension at 72° C. and a final extension at 72° C. for 5 min. The PCR product was isolated and purified from the PCR reaction mixture and cloned to pCR®4Blunt-TOPO®-vector according to the manufacturer's instructions (Invitrogen, USA). The insert was characterized by sequencing and the nucleotide sequence contained a partial coding region of an unknown gene. The deduced amino acid sequence of the partial gene showed similarity to a published hypothetical protein from *Chaetomium globosum* with Accession number XP_001219904. The hypothetical protein XP_001219904 is similar to family GH61 proteins. Thus the unknown gene is named Ma_cel61a.

The obtained PCR fragments chosen to be used as probes for cloning of the full-length genes from the *Acremonium thermophilum* ALKO4245 and *Melanocarpus albomyces* ALKO4237 strains are presented in Table 4.

TABLE 4

Probes chosen for cloning of the full-length cel61 genes from strains *Acremonium thermophilum* ALKO4245 and *Melanocarpus albomyces* ALKO4237. The genomic template DNA, primers used in the PCR reactions, size of the PCR fargments obtained, the name of the plasmid containing the probe fragment and SEQ ID NOs of the probe sequences are shown.

| Genomic DNA used as a template in PCR reaction | Primers | PCR fragment obtained (bp) | Insert in plasmid | SEQ ID NO: |
|---|---|---|---|---|
| ALKO4245 | FIB54, FIB57 | 349 bp | pALK3374 | 17 |
| ALKO4237 | FIB99, FIB101 | 239 bp | pALK3378 | 18 |
| ALKO4237 | FIB38, FIB35 | 860 bp | pALK2992 | 19 |

The pCR®4-TOPO® plasmid containing the PCR amplified probe for cloning the full-length gene encoding At_GH61 was named pALK3374 and the *E. coli* strain including this plasmid, RF9150, was deposited to the DSM collection under the accession number DSM25496. The pCR®4-TOPO® plasmid containing the PCR amplified probe for gene Ma_cel61a was named pALK2992 and the *E. coli* strain including this plasmid, RF9002, was deposited to the DSM collection under the accession number DSM25494. The pCR®4-TOPO® plasmid containing the PCR amplified probe for cloning the full-length gene encoding Ma_GH61B was named pALK3378 and the *E. coli* strain including this plasmid, RF9537 was deposited to the DSM collection under the α-cession number DSM25498.

*Acremonium thermophilum* ALKO4245 and *Melanocarpus albomyces* ALKO4237 genomic DNAs were digested with several restriction enzymes for Southern blot analysis. The probes for the hybridizations were the PCR fragments having SEQ ID NO: 17, SEQ ID NO: 18 and SEQ ID NO: 19 cut with EcoRI digestion or PCR amplified from the plasmids pALK3374, pALK2992 and pALK3378, respectively. The above probes were labeled by using digoxigenin according to supplier's instructions (Roche, Germany). Hybridizations were performed over night at 65° C. After hybridization the filters were washed 2×5 min at RT using 2×SSC–0.1% SDS followed by 2×15 min at 65° C. using 0.1×SSC–0.1% SDS.

From the genomic DNA of *Acremonium thermophilum* ALKO4245, an approximately 4.5 kb XbaI-digested fragment was obtained. From the genomic DNA of *Melanocarpus albomyces* ALKO4237, an approximately 5 kb BamHI-digested fragment was obtained with the dioxigenin-labeled probe fragment from plasmid pALK2992. Correspondingly, about 3.5 kb XhoI-digested fragment was obtained with the dioxigenin-labeled probe fragment from plasmid pALK3378 from the genomic DNA of the *Melanocarpus albomyces* ALKO4237. The hybridized genomic DNA fragments were isolated from the pool of the digested genomic fragments based on their size. The genomic fragments were isolated from agarose gel and were cloned to pBluescript II KS+ (Stratagene, CA, USA) vectors cleaved with XbaI, BamHI or XhoI. Ligation mixtures were transformed to *Escherichia coli* XL10-Gold cells (Stratagene, CA, USA) and plated on LB (Luria-Bertani) plates containing 50-100 µg/ml ampicillin. The *E. coli* colonies were screened for positive clones using colonial hybridization with the pALK3374, pALK2992 and pALK3378 inserts as probes in the hybridization conditions correspondingly to that described above for Southern blot analyses. Several positive clones were collected from the plates. They were shown by restriction digestion to contain inserts of expected sizes and the inserts were further screened using Southern hybridization with the pALK3374, pALK2992 and pALK3378 inserts as a probe. Southern blot was performed on inserts of the collected clones with hybridization performed at 68° C. and washed 2×5 min at RT using 2×SSC–0.1% SDS followed by 2×15 min at 68° C. using 0.1×SSC–0.1% SDS.

The full-length gene encoding the *Acremonium thermophilum* ALKO4245 protein At_GH61 was sequenced from the 4.5 kb XbaI insert and the plasmid containing this insert was named pALK3375. The *E. coli* strain RF9319 including the plasmid pALK3375 was deposited to the DSM collection under the accession number DSM25497. The gene encoding the *Acremonium thermophilum* ALKO4245 protein At_GH61 is named as At_cel61 (SEQ ID NO: 20). Correspondigly, the full-length gene encoding the *Melanocarpus albomyces* ALKO4237 Ma_GH61B was sequenced from the 3.5 kb XhoI insert and the plasmid containing this insert was named pALK3379. The *E. coli* strain RF9696 including the plasmid pALK3379 was deposited to the DSM collection under the accession number DSM25499. The gene encoding the *Melanocarpus albomyces* ALKO4237 protein Ma_GH61B is named as Ma_cel61b (SEQ ID NO: 22). The full-length gene Ma_cel61a (SEQ ID NO: 21) was sequenced from the *Melanocarpus albomyces* ALKO4237 5 kb BamHI insert and the plasmid containing this insert was named pALK2993. The partial cel61 sequence found in the pALK2992 insert (SEQ ID NO: 18) was included in the full-length Ma_cel61a gene sequence (SEQ ID NO: 21) obtained from the cloning. The *E. coli* strain RF9091 including the plasmid pALK2993 was deposited to the DSM collection under the accession number DSM25495. The relevant information on the gene sequences (SEQ ID NOs: 20-22) is summarized in Table 5.

TABLE 5

The summary on the cel61 genes isolated from *Acremonium thermophilum* ALKO4245 and *Melanocarpus albomyces* ALKO4237. The gene lengths with and without introns and the SEQ ID NOs of the genes are shown.

| Gene | Length with introns (bp)[a] | Coding region (bp)[b] | No of putative introns | Lengths of putative introns (bp) | SEQ ID NO: |
|---|---|---|---|---|---|
| At_cel61 | 1472 | 984 | 4 | 202, 140, 41, 102 | 20 |
| Ma_cel61a | 891 | 738 | 2 | 65, 85 | 21 |
| Ma_cel61b | 733 | 675 | 1 | 55 | 22 |

[a] The STOP codon is included.
[b] The STOP codon is not included.

The deduced amino acid sequence of the gene At_cel61 included the sequences of the At_GH61 peptides 1669,824 (SEQ ID NO: 1), 1763,938 (SEQ ID NO: 2), 431.7752 (SEQ ID NO: 3), 882.9711 (SEQ ID NO: 4) and 855.9166 (SEQ ID NO: 5) (Table 2). This confirms that the gene At_cel61 obtained from the cloning is the gene encoding the purified At_GH61 protein. The deduced amino acid sequence of gene Ma_cel61b included the sequences of the Ma_GH61B peptides #4349 (SEQ ID NO: 6), 2130,813 (SEQ ID NO: 7), 1283,527 (SEQ ID NO: 8), 2131,948 (SEQ ID NO: 9) and 4466,106 (SEQ ID NO: 10) (Table 2). This confirms that the gene Ma_cel61b obtained from the cloning is the gene encoding the purified Ma_GH61B protein. The relevant information on the deduced protein sequences (SEQ ID NOs: 23-25) is summarized in Table 6. The protein deduced from the gene sequence Ma_cel61a is named Ma_GH61A.

TABLE 6

The summary of the amino acid sequences deduced from the cel61 gene sequences from *Acremonium thermophilum* ALKO4245 and *Melanocarpus albomyces* ALKO4237.

| Gene | Protein | No of aas | Length of ss[a] | CBD[b] | Predicted MW (Da)[c] | Predicted pI[c] | SEQ ID NO: |
|---|---|---|---|---|---|---|---|
| At_cel61 | At_GH61 | 328 | 18 | Q296 to L328 | 32366 | 5.69 | 23 |
| Ma_cel61a | Ma_GH61A | 246 | 17 | — | 24649 | 4.97 | 24 |
| Ma_cel61b | Ma_GH61B | 225 | 17 | — | 22865 | 6.23 | 25 |

[a] The prediction on the signal sequence was made using the program SignalP V3.0 (Nielsen et al., 1997; Nielsen and Krogh, 1998; Bendtsen et al., 2004).
[b] The cellulose-binding domain (CBD), the amino acids of the CBD region are indicated [M1(Met #1) included in numbering].
[c] The predicted signal sequence was not included. The prediction was made using the Clone Manager 9 programme.

The comparison of the deduced GH61 sequences from *Acremonium thermophilum* ALKO4245 and *Melanocarpus albomyces* ALKO4237 to the sequences found from databases are shown in Table 7.

TABLE 7

The highest identity sequences to the deduced GH61 amino acid sequences from *Acremonium thermophilum* ALKO4245 and *Melanocarpus albomyces* ALKO4237. The full-length amino acid sequences including the signal sequences were aligned. The database search was performed at http://www.ebi.ac.uk/Tools/sss/fasta/ using FASTA (EMBL-EBI, FASTA - Protein Similarity Search, UniProt Knowledgebase and NRPL 1, BLOSUM50, Gap open −10, Gap, extend −2) and EMBOSS Needle (EMBL-EBI, EMBOSS-Needle - Pairwise Sequence Alignment, BLOSUM50, Gap open 10, gap extend 0.5) at http://www.ebi.ac.uk/Tools/psa/emboss_needle/ was used for determining the degree of identity.

| Organism and accession number | Identity (%) |
|---|---|
| At_GH61 | 100 |
| *Thielavia terrestris*, AEO68023 | 74.0 |

TABLE 7-continued

The highest identity sequences to the deduced GH61 amino acid sequences from *Acremonium thermophilum* ALKO4245 and *Melanocarpus albomyces* ALKO4237. The full-length amino acid sequences including the signal sequences were aligned. The database search was performed at http://www.ebi.ac.uk/Tools/sss/fasta/ using FASTA (EMBL-EBI, FASTA - Protein Similarity Search, UniProt Knowledgebase and NRPL 1, BLOSUM50, Gap open −10, Gap, extend −2) and EMBOSS Needle (EMBL-EBI, EMBOSS-Needle - Pairwise Sequence Alignment, BLOSUM50, Gap open 10, gap extend 0.5) at http://www.ebi.ac.uk/Tools/psa/emboss_needle/ was used for determining the degree of identity.

| Organism and accession number | Identity (%) |
|---|---|
| Ma_GH61A | 100 |
| WO2009085868, SEQ ID NO: 2 | 77.6 |
| Ma_GH61B | 100 |
| *Chaetomium globosum*, EAQ87022 | 78.2 |
| *Myceliophthora thermophila*, AEO61304 | 77.8 |

Example 4

Production of Recombinant GH61 Proteins in *Trichoderma reesei*

Expression plasmids were constructed for production of recombinant GH61 proteins from *Acremonium thermophilum* ALKO4245 and *Melanocarpus albomyces* ALKO4237 in *Trichoderma reesei*. The recombinant cel61 genes, including their own signal sequences, were exactly fused to the *T. reesei* cbh1/cel7A promoter by PCR. A BamHI site was created after the stop codon by PCR to fuse the gene at the 3″-end to the *T. reesei* cbh1/cel7A terminator. This leaves no original terminator in the constructs prior to the cbh1 terminator sequence. The *A. nidulans* amdS marker gene was used for selection of the transformants as described in Paloheimo et al. (2003). The linear expression cassettes (FIG. 1) were isolated from the vector backbones after NotI digestion. The expression cassettes of At_cel61 (6.8 kb), Ma_cel61a (6.2 kb) and Ma_cel61b (6.1 kb) were transformed into *T. reesei* protoplasts. The host strain used does not produce any of the four major *T. reesei* cellulases (CBHI, CBHI, EGI, EGII). The transformations were performed as in Penttilä et al. (1987) with the modifications described in Karhunen et al. (1993), selecting acetamide as a sole nitrogen source (amdS marker gene). The transformants were purified on selection plates through single conidia prior to sporulating them on PD.

The GH61 protein production of the transformants was analysed from the culture supernatans of the shake flask cultivations. The transformants were inoculated from the PD slants to shake flasks containing 50 ml of complex lactose-based cellulase inducing medium (Joutsjoki et al., 1993) buffered with 5% $KH_2PO_4$. The GH61 protein production was analyzed after cultivation for 7 days at 30° C., 250 rpm. Heterologous production of recombinant proteins was analyzed by SDS-PAGE with subsequent Coomassie staining. The genotypes of the chosen transformants were confirmed by Southern blot analyses in which genomic digests were included and the respective expression cassette was used as a probe.

The best-producing transformants were chosen to be cultivated in laboratory scale bioreactors at 28° C. in the cellulase inducing complex medium for 3-4 days with pH control 5.5±0.2 or 6.0±0.2 ($NH_3/H_3PO_4$) to obtain material for the application tests. The supernatants were recovered by centrifugation and filtering through Seitz-K 150 and EK filters (Pall SeitzSchenk Filtersystems GmbH, Bad Kreuznach, Germany).

Example 5

Hydrolysis of Hardwood Substrate with Enzyme Preparations Comprising Recombinant GH61 Proteins Steam exploded hardwood was suspended in 0.05 M sodium citrate buffer, pH 4.8. The final weight of the hydrolysis mixture was 1 g of which the total solids concentration was 12% (w/w). The substrate was hydrolysed using different enzyme mixtures at a dosage of 2 mg of protein per gram of total solids in 2 ml reaction tubes. The protein contents of the enzyme components were determined using the Pierce BCA assay kit, Product number 23227 (Thermo Scientific, MA, USA) with Bovine Serum Albumin, Product number 23209 (Thermo Scientific, MA, USA) as standard. The reaction tubes were agitated in a linear-shaking waterbath 1086 from GFL adjusted in different temperatures. For each sample point, a sample of 0.5 ml was taken from duplicate reaction tubes and centrifuged. The supernatant was boiled for 20 minutes to terminate the enzymatic hydrolysis, and analysed for reaction products from the hydrolysis.

A basis mixture of different cellulases was prepared using the following components:

CBHI/Cel7A preparation containing recombinant *Acremonium thermophilum* ALKO4245 CBHI/Cel7A (WO2007071818), CBHII/Cel6A preparation containing recombinant *Acremonium thermophilum* ALKO4245 CBHII/Cel6A (WO2011080317), EGII/Cel5A preparation containing recombinant *Thermoascus aurantiacus* ALKO4242 EGII/Cel5A (WO2007071818) with genetically attached CBM of *Trichoderma reesei* EGII/Cel5A (WO2007071818), Mesophilic EGI/Cel7B preparation containing recombinant *Trichoderma reesei* EGI/Cel7B, β-glucosidase preparation containing *Acremonium thermophilum* ALKO4245 β-glucosidase/Cel3A (WO2007071818), xylanase preparation containing *Thermoascus aurantiacus* ALKO4242 Xyn10A xylanase (WO2007071818).

All cellulases were heterologously produced as monocomponents in *Trichoderma reesei* host strain having cellulase-free background (the genes encoding the four major cellulases CBHI/Cel7A, CBHII/Cel6A, EGI/Cel7B and EGII/Cel5A were deleted). Crude culture supernatants were used in the mixture. The enzyme components were combined as follows to prepare a basis mixture: cellobiohydrolase CBHI/Cel7A preparation 61.1%, cellobiohydrolase CBHII/Cel6A preparation 15.3%, endoglucanase EGII/Cel5A preparation 10.2%, endoglucanase EGI/Cel7B preparation 8.2%, xylanase Xyn10A preparation 3% and β-glucosidase βG/Cel3A preparation 2.2%. This enzyme mixture was designated as MIXTURE 1.

For testing GH61 molecule performance in the hydrolysis three separate mixture combinations were prepared containing 90% of MIXTURE 1 and 10% of GH61 components:

GH61 protein preparation containing *Acremonium thermophilum* At_GH61.

GH61 enzyme preparation containing *Melancarpus albomyces* Ma_GH61A.

GH61 enzyme preparation containing *Thielavia terrestris* Tt_GH61E, a GH61 protein known in the art and described in Harris et al. (2010), Accession number ACE10234.

The mixtures containing GH61 proteins At_GH61, Ma_GH61A and Tt_GH61E were designated as MIXTURE 1_AT, MIXTURE 1_MA and MIXTURE 1_TT, respectively.

Figure 2:
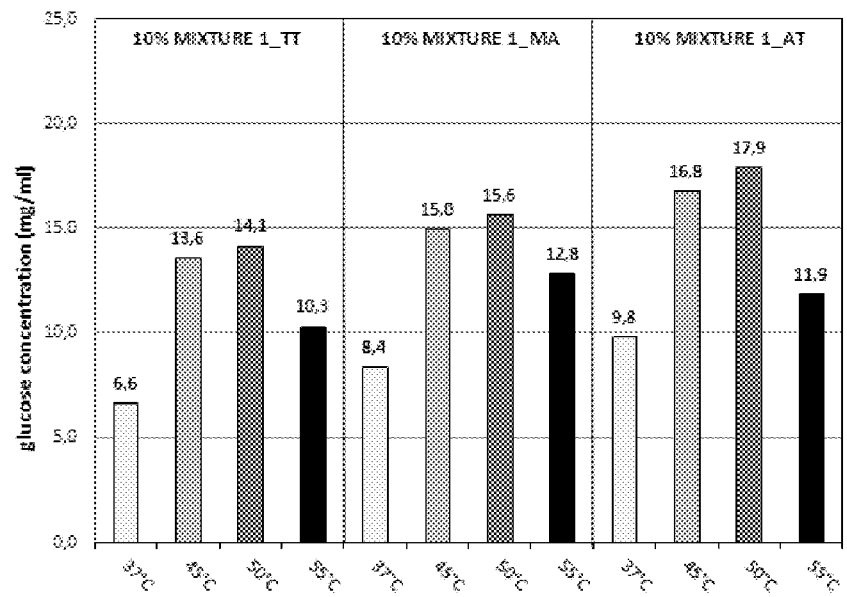
FIG. 2 shows results from hydrolysis of steam exploded hardwood performed with enzyme mixtures comprising the GH61 proteins of the invention. The hardwood substrate with 12% dry matter was hydrolyzed using different enzyme mixtures at a dosage of 2 mg of protein per gram of total solids at 37° C., 45°, 50° and 55° C. Enzyme mixtures containing GH61 proteins *Thielavia terrestris* Tt_GH61E (MIXTURE 1_TT), *Acremonium thermophilum* At_GH61 (MIXTURE 1_AT) and *Melanocarpus albomyces* Ma_GH61A (MIXTURE 1_MA) were used. Detailed compositions of the enzyme mixtures MIXTURE 1 and compositions comprising the tested GH61 proteins are described in Example 5. Samples from duplicate tubes were taken after 72 hours hydrolysis time and quantified by HPLC, in which the concentration of glucose was determined.

For all mixtures the hydrolysis was performed at 37° C., 45° C., 50° C. and 55° C. Samples were taken from the hydrolysis after 72 h, quantified by HPLC and the concentration of glucose was determined (FIG. 2).

The results show better performance of the MIXTURE 1_AT and MIXTURE 1_MA at all tested temperatures (37° C., 45° C., 50° C. and 55° C.) in comparison to the control MIXTURE 1_TT. At 55° C. the MIXTURE 1_MA and MIXTURE 1_AT performed 24% and 16% better than the control mix MIXTURE 1_TT. The amounts of sugars released from the hardwood substrate with the MIXTURE 1_AT and MIXTURE 1_MA were found to increase 27% and 11% in comparison to the control mix MIXTURE 1_TT at 50° C. At 45° C. the enzyme MIXTURE 1_AT and MIXTURE 1_MA were found to perform 24% and 10% better than the control mix MIXTURE 1_TT. At 37° C. MIXTURE 1_AT and MIXTURE 1_MA performed 48% and 27% better than the control mix MIXTURE 1_TT.

Example 6

Removal of Fibrous Residues from Automatic Dishwasher Filters with Enzyme Preparations Comprising Recombinant GH61 Proteins Hydrolysis of fibrous residues building up in automatic dishwashers was measured with ground fibers from apples, oranges and wheat suspended in dilute citrate buffer, pH 4.0 containing ca. 0.5% propylene glycol in 500 ml shake flasks. Equal amount of each fiber was added and the final total solids concentration was 4 g per liter. Enzymes were added at a dosage of 25 mg of protein per gram of total solids. The amount of protein from the enzyme preparations was determined by Bio-Rad protein assay (Bio-Rad Laboratories, Hercules, Calif., USA) using bovine gammaglobulin (Bio-Rad Laboratories, Hercules, Calif., USA) as standard. The flasks containing fibers and enzymes in dilute citrate buffer were heated to 50° C. in 230 rpm shaking. After 60 min incubation time at 50° C., the solution was filtered through a 200 μm mesh and the fibers left on the sieve dried for at least 20 h at 50° C. The dried fibers were weighed to measure the weight loss of the fibers. Weight loss was calculated as percentage of the weight of a blank. The blank containing fiber alone in the buffer (no enzymes) was prepared identically to the other samples.

Basic *Trichoderma reesei* cellulase mixture (Roal Oy, a classical *T. reesei* enzyme product) was used in the comparison. Enzyme mixtures contained basic *T. reesei* cellulase mixture alone (control) or a mixture containing 72% (18 mg) of *T. reesei* cellulase mixture and 28% (7 mg) of At_GH61 or Ma_GH61A for testing GH61 performance in the hydrolysis. The GH61 proteins were heterologously produced as monocomponents in *Trichoderma reesei* host strain having cellulase-free background (the genes encoding the four major cellulases CBHI, CBHII, EGI and EGII were deleted). Crude culture supernatants were used in the enzyme mixtures.

Figure 3:
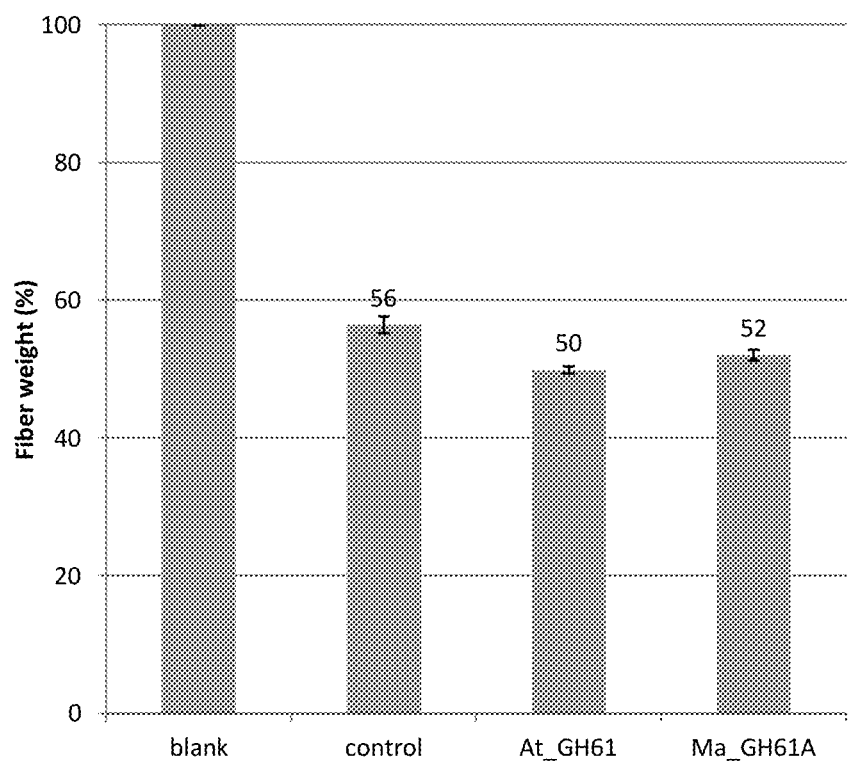
FIG. 3 shows results from hydrolysis of ground apple/orange/wheat fibre mixture performed with enzyme mixtures comprising the GH61 proteins of the invention. The test was performed in dilute citrate buffer, pH 4.0 containing ca. 0.5% (w/w) propylene glycol with an equal amount of each fiber at final total solids concentration of 4 g per liter. Enzymes were added at a dosage of 25 mg of protein per gram of total solids in 500 ml shake flasks. Basic *Trichoderma reesei* cellulase mixture (Roal Oy) was used as a control. The blank did not contain any added enzyme. Percentage of fiber weight after 60 min hydrolysis at 50° C. is presented for the control and mixtures containing 72%

The average results from triplicate samples of the control and samples containing the GH61 proteins are shown in FIG. 3. The weight of the fiber residues left in the sieve was found to decrease 11% and 7% by partly replacing the basic *T. reesei* cellulase mixture with *Acremonium thermophilum* At_GH61 or *Melanocarpus albomyces* Ma_GH61A proteins, respectively. The results show, thus, better performance when the *T. reesei* cellulase mixture is supplemented with GH61 protein At_GH61 or Ma_GH61A.

REFERENCES

Badger P C. (2002) Ethanol from cellulose: a general review. In Trends in new crops and new uses. J. Janick and A. Whipkey (eds.). ASHS Press, Alexandria, Va., USA, p. 17-21.

Bendtsen J D, Nielsen H, von Heijne G, and Brunak S. (2004) Improved prediction of signal peptides: SignalP 3.0. J. Mol. Biol. 340:783-795.

Bolton E T, and McCarthy B J. (1962) PNAS 84:1390 as presented in Sambrook, Fritsch and Maniatis, Molecular Cloning, p. 11.46 (1989).

Coen D M. (2001) The polymerase chain reaction. In: Ausubel F M., Brent R., Kingston R E., More D D., Seidman J G., Smith K. and Struhl K. (eds.) Current protocols in molecular biology. John Wiley & Sons. Inc., Hoboken, USA.

Gellissen G. (ed.) (2005) Production of recombinant proteins. Novel microbial and eukaryotic expression systems. Wiley-VCH Verlag Gmbh&Co. Weinheim, Germany.

Harris P V, Weiner D, McFarland K C, Re E, Navarro Poulsen J-C, Brown K, Salbo R, Ding H, Vlasenko E, Merino S, Xu F, Chemy J, Larsen S Y, and Leggio L L. (2010) Stimulation of lignocellulosic biomass hydrolysis by proteins of glycoside hydrolase family 61: structure and function of a large, enigmatic family. Biochemistry 49 (15): 3305-3316.

Henrissat B. (1991) A classification of glycosyl hydrolases based on amino acid sequence similarities. Biochem. J. 280: 309-316.

Henrissat B, and Bairoch A. (1993) New families in the classification of glycosyl hydrolases based on amino acid sequence similarities. Biochem. J. 293: 781-788.

Henrissat B, and Bairoch A. (1996). Updating the sequence-based classification of glycosyl hydrolases. Biochem. J. 316: 695-696.

Joutsjoki V V, Torkkeli T K, and Nevalainen K M H. (1993) Transformation of *Trichoderma reesei* with the *Hormoconis resinae* glucoamylase P (gamP) gene: production of a heterologous glucoamylase by *Trichoderma reesei*. Curr. Genet. 24: 223-228.

Karhunen T, Mäntylä M, Nevalainen K M H, and Suominen P L. (1993) High frequency one-step gene replacement in *Trichoderma reesei*. I. Endoglucanase I overproduction. Mol. Gen. Genet. 241: 515-522.

Needleman S, and Wunsch C. (1970) A general method applicable to the search for similarities in the amino acid sequence of two proteins. Journal of Molecular Biology 48, 443-453.

Nielsen H, Engelbrecht J, Brunak S, and von Heijne G. (1997) Identification of prokaryotic and eykaryotic signal peptides and prediction of their cleavage sites. Protein. Eng. 10:1-6.

Nielsen H, and Krogh A. (1998) Prediction of signal peptides and signal anchors by a hidden Markov model. In: Proceedings of the Sixth International Conference on Intelligent Systems for Molecular Biology (ISMB 6), AAAI Press, Menlo Park, Calif., p. 122-130.

Paloheimo M, Mantyla A, Kallio J, and Suominen P. (2003) High-yield production of a bacterial xylanase in the filamentous fungus *Trichoderma reesei* requires a carrier polypeptide with an intact domain structure. Appl. Env. Microbiol. 69: 7073-7082.

Penttilä M, Nevalainen H, Rättö M, Salminen E, and Knowles J. (1987) A versatile transformation system for the cellulolytic filamentous fungus *Trichoderma reesei*. Gene 61: 155-164.

Poutanen M, Salusjärvi L, Ruohonen L, Penttilä M, and Kalkkinen N. (2001) Use of matrix-assisted laser desorption/ionization time-of-flight mass mapping and nanospray liquidchromatography/electrospray ionization tandem mass spectrometry sequence tag analysis for high sensitivity identification of yeast proteins separated by two-dimensional gel electrophoresis. Rapid Commun. Mass Spectrom. 15: 1685-1692.

Raeder U, and Broda P. (1985) Rapid preparation of DNA from filamentous fungi. Lett. Appl. Microbiol. 1: 17-20.

Sambrook J, Fritsch E F, and Maniatis T. (1989) Molecular cloning, a laboratory manual. Cold Spring Harbor Laboratory, New York, US.

Sambrook J, and Russell D W. (2001) Molecular cloning, a laboratory manual. Cold Spring Harbor Laboratory, New York, US.

Shevchenko A, Wilm M, Vorm O, and Mann M. (1996) Mass spectrometric sequencing of proteins from silver-stained polyacrylamide gels. Anal. Chem. 68: 850-858.

Visser H, Joosten V, Punt P J, Gusakov A V, Olson P T, Joosten R, Bartels J, Visser J, Sinitsyn A P, Emalfarb M A, Verdoes J C, and Wery J. (2011) Development of a mature fungal technology and production platform for industrial enzymes based on the Myceliphthora thermophile isolate, reviously known as *Chrysosporium lucknowense* C1. Industrial Biotechology. 7: 214-223.

The invention claimed is:

1. An enzyme preparation comprising a GH61 polypeptide comprising an amino acid sequence having at least 95% sequence identity to SEQ ID NO: 23, SEQ ID NO: 24 or SEQ ID NO: 25 capable of enhancing hydrolysis of cellulosic material in a spent culture medium, wherein the enzyme preparation further comprising additives.

2. The enzyme preparation of claim 1, wherein the GH61 polypeptide is obtainable from *Acremonium thermophilum*.

3. The enzyme preparation of claim 1, further comprising at least one enzyme selected from the group consisting of cellobiohydrolase, endoglucanase, beta-glucosidase, beta-glucanase, xyloglucanase, xylanase, beta-xylosidase, cellobiose dehydrogenase, mannanase, beta-mannosidase, α-glucuronidase, acetyl xylan esterase, α-arabinofuranosidase, α-galactosidase, pectinase, endo-α-L-arabinase, exo-α-L-arabinases, endo-galactoronase, exo-galactoronase, endopectinlyase, pectate lyase, pectinesterase, phenol esterase, ligninase, lignin peroxidase, manganese-dependent peroxidase, $H_2O_2$-generating enzyme, laminarinase, chitosanase, ferulic acid esterase and laccase.

4. A method for treating cellulosic material, wherein the method comprises reacting the cellulosic material with a GH61 polypeptide of claim 1 or an enzyme preparation thereof.

5. A method according to claim 4, wherein the method comprises cleaning the interior of a dishwasher by contacting at least part of the interior of the dishwasher with the polypeptide of claim 1 or an enzyme preparation thereof.

6. The method of claim 4, wherein the cellulosic material is textile material, plants used in animal feed, or wood-derived pulp or secondary fiber.

7. Method of using a polypeptide according to claim 1, or an enzyme preparation thereof for processing biomass, and in biofuel, starch, textile, detergent, pulp and paper, food, feed or beverage industry, wherein the method comprises reacting the biomass, biofuel, starch, textile, detergent, pulp and paper, food, feed or beverage with a GH61 polypeptide of claim 1 or an enzyme preparation thereof.

8. Method of using according to claim 7 for biofinishing textile materials like fabrics or garments or yarn, wherein the method comprises reacting the textile materials like fabrics or garments or yarn with a GH61 polypeptide of claim 1 or an enzyme preparation thereof.

9. Method of using according to claim 7 for biostoning of denim, wherein the method comprises reacting the denim with a GH61 polypeptide of claim 1 or an enzyme preparation thereof.

10. Method of using according to claim 7 for cleaning the interior of a dishwashing machine, wherein the method comprises cleaning the interior of a dishwashing machine by contacting at least part of the interior of the dishwashing machine with a GH61 polypeptide of claim 1 or an enzyme preparation thereof.

11. A detergent composition comprising the enzyme preparation of claim 1.

12. A detergent composition according to claim 11, wherein the composition is a dishwashing machine cleaning composition.

13. A method for improving fabric care properties or textile cleaning effect of a detergent composition, comprising adding a polypeptide of claim 1 or an enzyme preparation thereof to the detergent composition.

14. Animal feed comprising the enzyme preparation of claim 1.

15. The enzyme preparation of claim 1, wherein the GH61 polypeptide has at least 95% identity to SEQ ID NO: 23, SEQ ID NO: 24 or SEQ ID NO: 25 or a fragment thereof capable of enhancing hydrolysis of cellulosic material.

16. The enzyme preparation of claim 1, wherein the GH61 polypeptide has at least 98% identity to SEQ ID NO: 23, SEQ ID NO: 24 or SEQ ID NO: 25 or a fragment thereof capable of enhancing hydrolysis of cellulosic material.

17. The enzyme preparation of claim 1, wherein the GH61 polypeptide is obtainable from *A. thermophilum* CBS 116240.

\* \* \* \* \*